US008710187B2

(12) United States Patent
Binz et al.

(10) Patent No.: US 8,710,187 B2
(45) Date of Patent: Apr. 29, 2014

(54) MODIFIED BINDING PROTEINS INHIBITING THE VEGF-A RECEPTOR INTERACTION

(75) Inventors: Hans Kaspar Binz, Birmensdorf (CH); Patrik Forrer, Dietikon (CH); Michael Tobias Stumpp, Geroldswil (CH)

(73) Assignee: Molecular Partners AG, Schlieren (CH)

( * ) Notice: Subject to any disclaimer, the term of this patent is extended or adjusted under 35 U.S.C. 154(b) by 0 days.

(21) Appl. No.: 13/643,618

(22) PCT Filed: Apr. 29, 2011

(86) PCT No.: PCT/EP2011/056824
§ 371 (c)(1),
(2), (4) Date: Oct. 31, 2012

(87) PCT Pub. No.: WO2011/135067
PCT Pub. Date: Nov. 3, 2011

(65) Prior Publication Data
US 2013/0116197 A1 May 9, 2013

(30) Foreign Application Priority Data
Apr. 30, 2010 (EP) ..................... 10161685

(51) Int. Cl.
*A61K 38/16* (2006.01)
*C07K 17/08* (2006.01)
*C07K 14/00* (2006.01)
*A61K 47/48* (2006.01)

(52) U.S. Cl.
CPC .............. *A61K 38/16* (2013.01); *C07K 14/00* (2013.01); *A61K 47/48215* (2013.01); *C07K 17/08* (2013.01)
USPC ............................ 530/350; 514/3.2; 514/21.2

(58) Field of Classification Search
CPC . A61K 38/00; A61K 47/48215; A61K 38/16; C07K 14/47; C07K 2319/74; C07K 17/08; C07K 14/00
See application file for complete search history.

(56) References Cited

U.S. PATENT DOCUMENTS

2006/0121045 A1* 6/2006 Iverson et al. ............. 424/164.1
2011/0207668 A1   8/2011 Binz et al.

FOREIGN PATENT DOCUMENTS

WO  00/75319      12/2000
WO  2010/060748   6/2010

OTHER PUBLICATIONS

Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Zahnd et al, A Designed Ankyrin Repeat Protein Evolved to Picomolar Affinity to Her2, J. Mol. Bio., 2007, 369, pp. 1015-1028.*
Lu et al, Effect of PEGylation on the Solution Conformation of Antibody Fragments, Journal of Pharmaceutical Sciences, 2008, 97, pp. 2062-2079.*
Definition of moiety, from http://dictionary.reference.com/browse/moiety, pp. 1-3, accessed Aug. 26, 2010.*
International Search Report issued Jul. 11, 2011 in International (PCT) Application No. PCT/EP2011/056824.
Ng, Eugene W.M., et al., "Anti-VEGF Aptamer (Pegaptanib) Therapy for Ocular Vascular Diseases", Annals of the New York Academy of Sciences, Jan. 1, 2006, pp. 151-171.
Stumpp, Michael T., et al., "DARPins: A new generation of protein therapeutics", Drug Discovery Today, vol. 13, Nos. 15-16, Aug. 1, 2008, pp. 695-701.
Vance, David, et al., "The design of polyvalent scaffolds for targeted delivery", Advanced Drug Delivery Reviews, vol. 61, No. 11, Sep. 30, 2009, pp. 931-939.
Sassa, Yukio, et al., "Antiangiogenic drugs in the management of ocular diseases: Focus on antivascular endothelial growth factor", Clinical Opthalmology, vol. 4, No. 1, Apr. 26, 2010, pp. 275-283.

* cited by examiner

Primary Examiner — Julie Ha
Assistant Examiner — Li Ni Komatsu
(74) Attorney, Agent, or Firm — Wenderoth, Lind & Ponack, L.L.P.

(57) ABSTRACT

The present invention relates to binding proteins specific for Vascular Endothelial Growth Factor A (VEGF-A), in particular to recombinant binding proteins comprising a polyethylene glycol moiety and a binding domain, which inhibits VEGF-Axxx (wherein xxx denotes the amino acid length of the VEGF-A mature protein) binding to Vascular Endothelial Growth Factor Receptor 2 (VEGFR-2). Examples of such recombinant binding proteins are proteins which comprise an ankyrin repeat domain with the desired binding specificity, and a polyethylene glycol moiety. The binding proteins are useful in the treatment of cancer and other pathological conditions, e.g. eye diseases such as age-related macular degeneration.

7 Claims, 5 Drawing Sheets

SEQUENCE LISTING

```
<160> NUMBER OF SEQ ID NOS: 9

<210> SEQ ID NO 1
<211> LENGTH: 1025
<212> TYPE: PRT
<213> ORGANISM: Artificial
<220> FEATURE:
<223> OTHER INFORMATION: synthetic construct, Ankyrin repeat protein

<400> SEQUENCE: 1

Gly Ser Asp Leu Gly Lys Lys Leu Leu Glu Ala Ala Arg Ala Gly Gln
1               5                   10                  15
```

```
Asp Asp Glu Val Arg Ile Leu Met Ala Asn Gly Ala Asp Val Asn Ala
             20                  25                  30

Phe Asp Trp Met Gly Trp Thr Pro Leu His Leu Ala Ala His Glu Gly
         35                  40                  45

His Leu Glu Ile Val Glu Val Leu Leu Lys Asn Gly Ala Asp Val Asn
 50                  55                  60

Ala Thr Asp Val Ser Gly Tyr Thr Pro Leu His Leu Ala Ala Ala Asp
 65                  70                  75                  80

Gly His Leu Glu Ile Val Glu Val Leu Leu Lys Tyr Gly Ala Asp Val
                 85                  90                  95

Asn Thr Lys Asp Asn Thr Gly Trp Thr Pro Leu His Leu Ser Ala Asp
            100                 105                 110

Leu Gly Arg Leu Glu Ile Val Glu Val Leu Leu Lys Tyr Gly Ala Asp
        115                 120                 125

Val Asn Ala Gln Asp Lys Phe Gly Lys Thr Ala Phe Asp Ile Ser Ile
    130                 135                 140

Asp Asn Gly Asn Glu Asp Leu Ala Glu Ile Leu Gln Lys Ala Ala Ser
145                 150                 155                 160

Gly Ser Pro Ala Gly Ser Pro Thr Ser Thr Glu Glu Gly Thr Ser Glu
                165                 170                 175

Ser Ala Thr Pro Glu Ser Gly Pro Gly Thr Ser Thr Glu Pro Ser Glu
            180                 185                 190

Gly Ser Ala Pro Gly Ser Pro Ala Gly Ser Pro Thr Ser Thr Glu Glu
        195                 200                 205

Gly Thr Ser Thr Glu Pro Ser Glu Gly Ser Ala Pro Gly Thr Ser Thr
    210                 215                 220

Glu Pro Ser Glu Gly Ser Ala Pro Gly Thr Ser Glu Ser Ala Thr Pro
225                 230                 235                 240

Glu Ser Gly Pro Gly Ser Glu Pro Ala Thr Ser Gly Ser Glu Thr Pro
                245                 250                 255

Gly Ser Glu Pro Ala Thr Ser Gly Ser Glu Thr Pro Gly Ser Pro Ala
            260                 265                 270

Gly Ser Pro Thr Ser Thr Glu Glu Gly Thr Ser Glu Ser Ala Thr Pro
        275                 280                 285

Glu Ser Gly Pro Gly Thr Ser Thr Glu Pro Ser Glu Gly Ser Ala Pro
    290                 295                 300

Gly Thr Ser Thr Glu Pro Ser Glu Gly Ser Ala Pro Gly Ser Pro Ala
305                 310                 315                 320

Gly Ser Pro Thr Ser Thr Glu Glu Gly Thr Ser Thr Glu Pro Ser Glu
                325                 330                 335

Gly Ser Ala Pro Gly Thr Ser Thr Glu Pro Ser Glu Gly Ser Ala Pro
            340                 345                 350

Gly Thr Ser Glu Ser Ala Thr Pro Glu Ser Gly Pro Gly Thr Ser Thr
        355                 360                 365

Glu Pro Ser Glu Gly Ser Ala Pro Gly Thr Ser Glu Ser Ala Thr Pro
    370                 375                 380

Glu Ser Gly Pro Gly Ser Glu Pro Ala Thr Ser Gly Ser Glu Thr Pro
385                 390                 395                 400

Gly Thr Ser Thr Glu Pro Ser Glu Gly Ser Ala Pro Gly Thr Ser Thr
                405                 410                 415

Glu Pro Ser Glu Gly Ser Ala Pro Gly Thr Ser Glu Ser Ala Thr Pro
            420                 425                 430

Glu Ser Gly Pro Gly Thr Ser Glu Ser Ala Thr Pro Glu Ser Gly Pro
        435                 440                 445
```

Gly Ser Pro Ala Gly Ser Pro Thr Ser Thr Glu Glu Gly Thr Ser Glu
            450                 455                 460

Ser Ala Thr Pro Glu Ser Gly Pro Gly Ser Glu Pro Ala Thr Ser Gly
465                 470                 475                 480

Ser Glu Thr Pro Gly Thr Ser Glu Ser Ala Thr Pro Glu Ser Gly Pro
                    485                 490                 495

Gly Thr Ser Thr Glu Pro Ser Glu Gly Ser Ala Pro Gly Thr Ser Thr
            500                 505                 510

Glu Pro Ser Glu Gly Ser Ala Pro Gly Thr Ser Thr Glu Pro Ser Glu
            515                 520                 525

Gly Ser Ala Pro Gly Thr Ser Thr Glu Pro Ser Glu Gly Ser Ala Pro
            530                 535                 540

Gly Thr Ser Thr Glu Pro Ser Glu Gly Ser Ala Pro Gly Thr Ser Thr
545                 550                 555                 560

Glu Pro Ser Glu Gly Ser Ala Pro Gly Ser Pro Ala Gly Ser Pro Thr
                    565                 570                 575

Ser Thr Glu Glu Gly Thr Ser Thr Glu Pro Ser Glu Gly Ser Ala Pro
            580                 585                 590

Gly Thr Ser Glu Ser Ala Thr Pro Glu Ser Gly Pro Gly Ser Glu Pro
            595                 600                 605

Ala Thr Ser Gly Ser Glu Thr Pro Gly Thr Ser Glu Ser Ala Thr Pro
610                 615                 620

Glu Ser Gly Pro Gly Ser Glu Pro Ala Thr Ser Gly Ser Glu Thr Pro
625                 630                 635                 640

Gly Thr Ser Glu Ser Ala Thr Pro Glu Ser Gly Pro Gly Thr Ser Thr
                    645                 650                 655

Glu Pro Ser Glu Gly Ser Ala Pro Gly Thr Ser Glu Ser Ala Thr Pro
            660                 665                 670

Glu Ser Gly Pro Gly Ser Pro Ala Gly Ser Pro Thr Ser Thr Glu Glu
            675                 680                 685

Gly Ser Pro Ala Gly Ser Pro Thr Ser Thr Glu Glu Gly Ser Pro Ala
            690                 695                 700

Gly Ser Pro Thr Ser Thr Glu Glu Gly Thr Ser Glu Ser Ala Thr Pro
705                 710                 715                 720

Glu Ser Gly Pro Gly Thr Ser Thr Glu Pro Ser Glu Gly Ser Ala Pro
                    725                 730                 735

Gly Thr Ser Glu Ser Ala Thr Pro Glu Ser Gly Pro Gly Ser Glu Pro
            740                 745                 750

Ala Thr Ser Gly Ser Glu Thr Pro Gly Thr Ser Glu Ser Ala Thr Pro
            755                 760                 765

Glu Ser Gly Pro Gly Ser Glu Pro Ala Thr Ser Gly Ser Glu Thr Pro
            770                 775                 780

Gly Thr Ser Glu Ser Ala Thr Pro Glu Ser Gly Pro Gly Thr Ser Thr
785                 790                 795                 800

Glu Pro Ser Glu Gly Ser Ala Pro Gly Ser Pro Ala Gly Ser Pro Thr
                    805                 810                 815

Ser Thr Glu Glu Gly Thr Ser Glu Ser Ala Thr Pro Glu Ser Gly Pro
            820                 825                 830

Gly Ser Glu Pro Ala Thr Ser Gly Ser Glu Thr Pro Gly Thr Ser Glu
            835                 840                 845

Ser Ala Thr Pro Glu Ser Gly Pro Gly Ser Pro Ala Gly Ser Pro Thr
850                 855                 860

Ser Thr Glu Glu Gly Ser Pro Ala Gly Ser Pro Thr Ser Thr Glu Glu

```
                865                 870                 875                 880
Gly Thr Ser Thr Glu Pro Ser Glu Gly Ser Ala Pro Gly Thr Ser Glu
                885                 890                 895
Ser Ala Thr Pro Glu Ser Gly Pro Gly Thr Ser Glu Ser Ala Thr Pro
            900                 905                 910
Glu Ser Gly Pro Gly Thr Ser Glu Ser Ala Thr Pro Glu Ser Gly Pro
            915                 920                 925
Gly Ser Glu Pro Ala Thr Gly Ser Glu Thr Pro Gly Ser Glu Pro
        930                 935                 940
Ala Thr Ser Gly Ser Glu Thr Pro Gly Ser Pro Ala Gly Ser Pro Thr
945                 950                 955                 960
Ser Thr Glu Glu Gly Thr Ser Thr Glu Pro Ser Glu Gly Ser Ala Pro
                965                 970                 975
Gly Thr Ser Thr Glu Pro Ser Glu Gly Ser Ala Pro Gly Ser Glu Pro
                980                 985                 990
Ala Thr Ser Gly Ser Glu Thr Pro  Gly Thr Ser Glu Ser  Ala Thr Pro
                995                 1000                1005
Glu Ser  Gly Pro Gly Thr Ser   Thr Glu Pro Ser Glu   Gly Ser Ala
    1010                1015                 1020
Pro Gly
    1025

<210> SEQ ID NO 2
<211> LENGTH: 168
<212> TYPE: PRT
<213> ORGANISM: Artificial
<220> FEATURE:
<223> OTHER INFORMATION: synthetic construct, Ankyrin repeat protein

<400> SEQUENCE: 2

Gly Ser Asp Leu Gly Lys Lys Leu Leu Glu Ala Ala Arg Ala Gly Gln
1               5                   10                  15
Asp Asp Glu Val Arg Ile Leu Met Ala Asn Gly Ala Asp Val Asn Ala
            20                  25                  30
Phe Asp Trp Met Gly Trp Thr Pro Leu His Leu Ala Ala His Glu Gly
        35                  40                  45
His Leu Glu Ile Val Glu Val Leu Leu Lys Asn Gly Ala Asp Val Asn
    50                  55                  60
Ala Thr Asp Val Ser Gly Tyr Thr Pro Leu His Leu Ala Ala Ala Asp
65                  70                  75                  80
Gly His Leu Glu Ile Val Glu Val Leu Leu Lys His Gly Ala Asp Val
                85                  90                  95
Asn Thr Lys Asp Asn Thr Gly Trp Thr Pro Leu His Leu Ser Ala Asp
            100                 105                 110
Leu Gly His Leu Glu Ile Val Glu Val Leu Leu Lys Asn Gly Ala Asp
        115                 120                 125
Val Asn Ala Gln Asp Lys Phe Gly Lys Thr Ala Phe Asp Ile Ser Ile
    130                 135                 140
Asp Asn Gly Asn Glu Asp Leu Ala Glu Ile Leu Gln Lys Ala Ala Gly
145                 150                 155                 160
Gly Gly Ser Gly Gly Gly Ser Cys
                165

<210> SEQ ID NO 3
<211> LENGTH: 135
<212> TYPE: PRT
<213> ORGANISM: Artificial
```

```
<220> FEATURE:
<223> OTHER INFORMATION: synthetic construct, Ankyrin repeat protein

<400> SEQUENCE: 3

Gly Ser Asp Leu Asp Lys Lys Leu Leu Glu Ala Ala Arg Ala Gly Gln
1               5                   10                  15

Asp Asp Glu Val Arg Ile Leu Met Ala Asn Gly Ala Asp Val Asn Ala
                20                  25                  30

Arg Asp Ser Thr Gly Trp Thr Pro Leu His Leu Ala Ala Pro Trp Gly
            35                  40                  45

His Pro Glu Ile Val Glu Val Leu Leu Lys Asn Gly Ala Asp Val Asn
        50                  55                  60

Ala Ala Asp Phe Gln Gly Trp Thr Pro Leu His Leu Ala Ala Ala Val
65                  70                  75                  80

Gly His Leu Glu Ile Val Glu Val Leu Leu Lys Tyr Gly Ala Asp Val
                85                  90                  95

Asn Ala Gln Asp Lys Phe Gly Lys Thr Ala Phe Asp Ile Ser Ile Asp
                100                 105                 110

Asn Gly Asn Glu Asp Leu Ala Glu Ile Leu Gln Lys Ala Ala Gly Gly
            115                 120                 125

Gly Ser Gly Gly Gly Ser Cys
        130                 135

<210> SEQ ID NO 4
<211> LENGTH: 540
<212> TYPE: PRT
<213> ORGANISM: Artificial
<220> FEATURE:
<223> OTHER INFORMATION: synthetic construct, Ankyrin repeat protein

<400> SEQUENCE: 4

Gly Ser Asp Leu Gly Lys Lys Leu Leu Glu Ala Ala Arg Ala Gly Gln
1               5                   10                  15

Asp Asp Glu Val Arg Ile Leu Met Ala Asn Gly Ala Asp Val Asn Thr
                20                  25                  30

Ala Asp Ser Thr Gly Trp Thr Pro Leu His Leu Ala Val Pro Trp Gly
            35                  40                  45

His Leu Glu Ile Val Glu Val Leu Leu Lys Tyr Gly Ala Asp Val Asn
        50                  55                  60

Ala Lys Asp Phe Gln Gly Trp Thr Pro Leu His Leu Ala Ala Ala Ile
65                  70                  75                  80

Gly His Gln Glu Ile Val Glu Val Leu Leu Lys Asn Gly Ala Asp Val
                85                  90                  95

Asn Ala Gln Asp Lys Phe Gly Lys Thr Ala Phe Asp Ile Ser Ile Asp
                100                 105                 110

Asn Gly Asn Glu Asp Leu Ala Glu Ile Leu Gln Lys Ala Ala Gly Ser
            115                 120                 125

Gly Ser Ala Ser Pro Ala Ala Pro Ala Pro Ala Ser Pro Ala Ala Pro
        130                 135                 140

Ala Pro Ser Ala Pro Ala Ala Ser Pro Ala Ala Pro Ala Pro Ala Ser
145                 150                 155                 160

Pro Ala Ala Pro Ala Pro Ser Ala Pro Ala Ala Ser Pro Ala Ala Pro
                165                 170                 175

Ala Pro Ala Ser Pro Ala Ala Pro Ala Pro Ser Ala Pro Ala Ala Ser
            180                 185                 190

Pro Ala Ala Pro Ala Pro Ala Ser Pro Ala Ala Pro Ala Pro Ser Ala
                195                 200                 205
```

Pro Ala Ala Ser Pro Ala Ala Pro Ala Pro Ser Pro Ala Ala Pro
          210                 215                 220

Ala Pro Ser Ala Pro Ala Ala Ser Pro Ala Ala Pro Ala Pro Ala Ser
225                 230                 235                 240

Pro Ala Ala Pro Ala Pro Ser Ala Pro Ala Ala Ser Pro Ala Ala Pro
                245                 250                 255

Ala Pro Ala Ser Pro Ala Ala Pro Ala Pro Ser Ala Pro Ala Ala Ser
                260                 265                 270

Pro Ala Ala Pro Ala Pro Ala Ser Pro Ala Ala Pro Ala Pro Ser Ala
                275                 280                 285

Pro Ala Ala Ser Pro Ala Ala Pro Ala Pro Ser Pro Ala Ala Pro
          290                 295                 300

Ala Pro Ser Ala Pro Ala Ala Ser Pro Ala Ala Pro Ala Pro Ala Ser
305                 310                 315                 320

Pro Ala Ala Pro Ala Pro Ser Ala Pro Ala Ala Ser Pro Ala Ala Pro
                325                 330                 335

Ala Pro Ala Ser Pro Ala Ala Pro Ala Pro Ser Ala Pro Ala Ala Ser
                340                 345                 350

Pro Ala Ala Pro Ala Pro Ala Ser Pro Ala Ala Pro Ala Pro Ser Ala
          355                 360                 365

Pro Ala Ala Ser Pro Ala Pro Ala Pro Ser Pro Ala Ala Pro
          370                 375                 380

Ala Pro Ser Ala Pro Ala Ala Ser Pro Ala Ala Pro Ala Pro Ala Ser
385                 390                 395                 400

Pro Ala Ala Pro Ala Pro Ser Ala Pro Ala Ala Ser Pro Ala Ala Pro
                405                 410                 415

Ala Pro Ala Ser Pro Ala Ala Pro Ala Pro Ser Ala Pro Ala Ala Ser
                420                 425                 430

Pro Ala Ala Pro Ala Pro Ala Ser Pro Ala Ala Pro Ala Pro Ser Ala
          435                 440                 445

Pro Ala Ala Ser Pro Ala Ala Pro Ala Pro Ser Pro Ala Ala Pro
          450                 455                 460

Ala Pro Ser Ala Pro Ala Ala Ser Pro Ala Ala Pro Ala Pro Ala Ser
465                 470                 475                 480

Pro Ala Ala Pro Ala Pro Ser Ala Pro Ala Ala Ser Pro Ala Ala Pro
                485                 490                 495

Ala Pro Ala Ser Pro Ala Ala Pro Ala Pro Ser Ala Pro Ala Ala Ser
                500                 505                 510

Pro Ala Ala Pro Ala Pro Ala Ser Pro Ala Ala Pro Ala Pro Ser Ala
          515                 520                 525

Pro Ala Ala Ser Pro Ala Ala Pro Ala Pro Ser
          530                 535                 540

<210> SEQ ID NO 5
<211> LENGTH: 135
<212> TYPE: PRT
<213> ORGANISM: Artificial
<220> FEATURE:
<223> OTHER INFORMATION: synthetic construct, Ankyrin repeat protein

<400> SEQUENCE: 5

Gly Ser Asp Leu Gly Lys Lys Leu Leu Glu Ala Ala Arg Val Gly Gln
1               5                   10                  15

Asp Asp Glu Val Arg Ile Leu Met Ala Asp Gly Ala Asp Val Asn Ala
                20                  25                  30

```
Ser Asp Phe Lys Gly Asp Thr Pro Leu His Leu Ala Ala Ser Gln Gly
        35                  40                  45

His Leu Glu Ile Val Glu Val Leu Leu Lys Tyr Gly Ala Asp Val Asn
 50                  55                  60

Ala Tyr Asp Met Leu Gly Trp Thr Pro Leu His Leu Ala Ala Asp Leu
 65                  70                  75                  80

Gly His Leu Glu Ile Val Glu Val Leu Leu Lys Tyr Gly Ala Asp Val
                 85                  90                  95

Asn Ala Gln Asp Arg Phe Gly Lys Thr Ala Phe Asp Ile Ser Ile Asp
                100                 105                 110

Asn Gly Asn Glu Asp Leu Ala Glu Ile Leu Gln Lys Ala Ala Gly Ser
            115                 120                 125

Pro Ser Thr Ala Asp Gly Cys
        130                 135
```

<210> SEQ ID NO 6
<211> LENGTH: 130
<212> TYPE: PRT
<213> ORGANISM: Artificial
<220> FEATURE:
<223> OTHER INFORMATION: synthetic construct, Ankyrin repeat protein

<400> SEQUENCE: 6

```
Gly Ser Asp Leu Gly Lys Lys Leu Leu Glu Ala Val Arg Ala Gly Gln
 1               5                  10                  15

Asp Asp Glu Val Arg Ile Leu Met Thr Asn Gly Ala Asp Val Asn Ala
                 20                  25                  30

Lys Asp Gln Phe Gly Phe Thr Pro Leu Gln Leu Ala Ala Tyr Asn Gly
        35                  40                  45

His Leu Glu Ile Val Glu Val Leu Leu Lys Tyr Gly Ala Asp Val Asn
 50                  55                  60

Ala Phe Asp Ile Phe Gly Trp Thr Pro Leu His Leu Ala Ala Asp Leu
 65                  70                  75                  80

Gly His Leu Glu Ile Val Glu Val Leu Leu Lys Asn Gly Ala Asp Val
                 85                  90                  95

Asn Ala Gln Asp Lys Phe Gly Arg Thr Ala Phe Asp Ile Ser Ile Asp
                100                 105                 110

Asn Gly Asn Glu Asp Leu Ala Glu Ile Leu Gln Lys Ala Ala Ser Gly
            115                 120                 125

Ser Cys
    130
```

<210> SEQ ID NO 7
<211> LENGTH: 168
<212> TYPE: PRT
<213> ORGANISM: Artificial
<220> FEATURE:
<223> OTHER INFORMATION: synthetic construct, Ankyrin repeat protein

<400> SEQUENCE: 7

```
Gly Ser Asp Leu Gly Lys Lys Leu Leu Glu Ala Ala Arg Ala Gly Gln
 1               5                  10                  15

Asp Asp Glu Val Arg Ile Leu Met Ala Asn Gly Ala Asp Val Asn Ala
                 20                  25                  30

Val Asp Tyr Ile Gly Trp Thr Pro Leu His Leu Ala Ala Ala Tyr Gly
        35                  40                  45

His Leu Glu Ile Val Glu Val Leu Leu Lys Tyr Ser Ala Asp Val Asn
 50                  55                  60
```

-continued

```
Ala Glu Asp Phe Ala Gly Tyr Thr Pro Leu His Leu Ala Ala Ser Asn
 65                  70                  75                  80

Gly His Leu Glu Ile Val Glu Val Leu Leu Lys Tyr Gly Ala Asp Val
                 85                  90                  95

Asn Thr Lys Asp Asn Thr Gly Trp Thr Pro Leu His Leu Ser Ala Asp
            100                 105                 110

Leu Gly His Leu Glu Ile Val Glu Val Leu Leu Lys Tyr Gly Ala Asp
        115                 120                 125

Val Asn Thr Gln Asp Lys Phe Gly Lys Thr Ala Phe Asp Ile Ser Ile
    130                 135                 140

Asp Asn Gly Asn Glu Asp Leu Ala Glu Ile Leu Gln Lys Ala Ala Gly
145                 150                 155                 160

Ser Pro Ser Thr Ala Asp Gly Cys
                165

<210> SEQ ID NO 8
<211> LENGTH: 9
<212> TYPE: PRT
<213> ORGANISM: Artificial
<220> FEATURE:
<223> OTHER INFORMATION: synthetic construct, Polypeptide linker

<400> SEQUENCE: 8

Gly Gly Gly Ser Gly Gly Gly Ser Cys
1               5

<210> SEQ ID NO 9
<211> LENGTH: 9
<212> TYPE: PRT
<213> ORGANISM: Artificial
<220> FEATURE:
<223> OTHER INFORMATION: synthetic construct, Polypeptide linker

<400> SEQUENCE: 9

Gly Ser Pro Ser Thr Ala Asp Gly Cys
1               5
```

MODIFIED BINDING PROTEINS INHIBITING THE VEGF-A RECEPTOR INTERACTION

CROSS-REFERENCE TO RELATED APPLICATION

The instant application is a National Phase application under 35 U.S.C. §371 of International Application No. PCT/EP11/56824 filed on Apr. 29, 2011 and claims priority to EP 10161685 filed on Apr. 30, 2010.

FIELD OF THE INVENTION

The present invention relates to modified recombinant binding proteins specific for VEGF-A, as well as pharmaceutical compositions comprising such proteins, and the use of such proteins in the treatment of tumors and eye diseases.

BACKGROUND OF THE INVENTION

Angiogenesis, the growth of new blood vessels from pre-existing vasculature, is a key process in several pathological conditions, including tumor growth and eye diseases, in particular ocular neovascularization diseases such as age-related macular degeneration (AMD) or diabetic macular edema (DME) (Carmeliet, P., Nature 438, 932-936, 2005). Vascular endothelial growth factors (VEGFs) stimulate angiogenesis and lymphangiogenesis by activating VEGF receptor (VEGFR) tyrosine kinases in endothelial cells (Ferrara, N., Gerber, H. P. and LeCouter, J., Nature Med. 9, 669-676, 2003).

The mammalian VEGF family consists of five glycoproteins referred to as VEGF-A, VEGF-B, VEGF-C, VEGF-D (also known as FIGF) and placenta growth factor (PlGF, also known as PGF). VEGF-A has been shown to be an effective target for anti-angiogenic therapy (Ellis, L. M. and Hicklin, D. J., Nature Rev. Cancer 8, 579-591, 2008). The VEGF-A ligands bind to and activate three structurally similar type III receptor tyrosine kinases, designated VEGFR-1 (also known as FLT1), VEGFR-2 (also known as KDR) and VEGFR-3 (also known as FLT4). The VEGF ligands have distinctive binding specificities for each of these tyrosine kinase receptors, which contribute to their diversity of function. In response to ligand binding, the VEGFR tyrosine kinases activate a network of distinct downstream signaling pathways. VEGFR-1 and VEGFR-2 are primarily found on the vascular endothelium whereas VEGFR-3 is mostly found on the lymphatic endothelium. These receptors all have an extracellular domain, a single transmembrane region and a consensus tyrosine kinase sequence interrupted by a kinase-insert domain. More recently neuropilin (NRP-1), originally identified as a receptor for the semaphorin/collapsin family of neuronal guidance mediators, was shown to act as an isoform specific receptor for VEGF-A.

Various isoforms of VEGF-A are known that are generated by alternative splicing from eight exons within the VEGF-A gene. All isoforms contain exons 1-5 and the terminal exon, exon 8. Exons 6 and 7, which encode heparin-binding domains, can be included or excluded. This gives rise to a family of proteins termed according to their amino acid number: VEGF-A165, VEGF-A121, VEGF-A189, and so on. Exon 8, however, contains two 3' splice sites in the nucleotide sequences, which can be used by the cell to generate two families of isoforms with identical length, but differing C-terminal amino acid sequences (Varey, A. H. R. et al., British J. Cancer 98, 1366-1379, 2008). VEGF-Axxx ("xxx" denotes the amino acid number of the mature protein), the pro-angiogenic family of isoforms, is generated by use of the most proximal sequence in exon 8 (resulting in the inclusion of exon 8a). The more recently described anti-angiogenic VEGF-Axxxb isoforms are generated by the use of a distal splice site, 66 bp further along the gene from the proximal splice site. This results in splicing out of exon 8a and the production of mRNA sequences that encode the VEGF-Axxxb family. VEGF-A165 is the predominant pro-angiogenic isoform and is commonly overexpressed in a variety of human solid tumors. VEGF-A165b was the first of the exon 8b-encoded isoforms identified and was shown to have anti-angiogenic effects (Varey et al., loc. cit.; Konopatskaya, O. et al., Molecular Vision 12, 626-632, 2006). It is an endogenous inhibitory form of VEGF-A, which decreases VEGF-A induced proliferation and migration of endothelial cells. Although it can bind to VEGFR-2, VEGF-A165b binding does not result in receptor phosphorylation or activation of the downstream signaling pathways.

There are several approaches to inhibiting VEGF-A signaling, including neutralization of the ligand or receptor by antibodies, and blocking VEGF-A receptor activation and signaling with tyrosine kinase inhibitors. VEGF-A targeted therapy has been shown to be efficacious as a single agent in AMD, DME, renal cell carcinoma and hepatocellular carcinoma, whereas it is of only of benefit when combined with chemotherapy for patients with metastatic colorectal, non-small-cell lung and metastatic breast cancer (Narayanan, R. et al., Nat. Rev. Drug Discov. 5, 815-816, 2005; Ellis and Hicklin, loc. cit).

Beside antibodies other binding domains can be used to neutralize a ligand or a receptor (Skerra, A., J. Mol. Recog. 13, 167-187, 2000; Binz, H. K., Amstutz, P. and Plückthun, A., Nat. Biotechnol. 23, 1257-1268, 2005). One such novel class of binding domains are based on designed repeat domains (WO 02/20565; Binz, H. K., Amstutz, P., Kohl, A., Stumpp, M. T., Briand, C., Forrer, P., Grütter, M. G., and Plückthun, A., Nat. Biotechnol. 22, 575-582, 2004). WO 02/20565 describes how large libraries of repeat proteins can be constructed and their general application. Nevertheless, WO 02/20565 does neither disclose the selection of repeat domains with binding specificity for VEGF-Axxx nor concrete repeat sequence motifs of repeat domains that specifically bind to VEGF-Axxx.

Targeting VEGF-A with currently available therapeutics is not effective in all patients, or for all diseases (e.g., EGFR-expressing cancers). It has even become increasingly apparent that the therapeutic benefit associated with VEGF-A targeted therapy is complex and probably involves multiple mechanisms (Ellis and Hicklin, loc. cit.). For example, marketed anti-VEGF drugs, such as bevacizumab (AVASTIN®) or ranibizumab (LUCENTIS®) (see WO 96/030046, WO 98/045331 and WO 98/045332) or drugs in clinical development, such as VEGF-TRAP® (aflibercept) (WO 00/075319) do not distinguish between the pro- and anti-angiogenic forms of VEGF-A, so they do inhibit both. As a result, they inhibit angiogenesis, but also deprive healthy tissues of an essential survival factor, namely VEGF-Axxxb, resulting in cytotoxicity and dose-limiting side effects, which in turn limit efficacy. Side effects common to current anti-VEGF-A therapies are gastrointestinal perforations, bleeding, hypertension, thromboembolic events and proteinuria (Kamba, T. and McDonald, D. M., Br. J. Cancer 96, 1788-95, 2007). Another marketed anti-VEGF drug for the treatment of AMD is pegaptanib (WO 98/018480; MACUGEN®, a registered trademark of Pfizer). Pegaptanib is a PEGylated anti-VEGF aptamer, a single strand of nucleic acid that binds with specificity to the target protein. For the treatment of neovascular AMD there is ample evidence that vision outcomes with LUCENTIS® (ranibizumab) are superior to those with MACUGEN® (pegaptanib), and there is no definitive evidence to suggest a difference in safety between the drugs. As a result, MACUGEN® (pegaptanib) is not a commonly used therapy for this disease.

Overall, a need exists for improved anti-angiogenic agents for treating cancer and other pathological conditions.

The technical problem underlying the present invention is to identify novel anti-angiogenic agents, such as repeat domains with binding specificity to VEGF-Axxx, for an improved treatment of cancer and other pathological conditions, e.g. eye diseases such as AMD or DME. The solution to this technical problem is achieved by providing the embodiments characterized in the claims.

SUMMARY OF THE INVENTION

The present invention relates to a recombinant binding protein comprising an ankyrin repeat domain and a polyethylene glycol moiety of at least 5 kDa molecular weight, wherein said ankyrin domain binds VEGF-Axxx with a Kd below $10^{-9}$ M and inhibits VEGF-Axxx binding to VEGFR-2.

In a preferred embodiment, the polyethylene glycol moiety is coupled to a single Cys residue of the binding domain.

The invention further relates to a pharmaceutical composition comprising one or more of the above mentioned binding proteins or nucleic acid molecules.

The invention further relates to a method of treatment of cancer and other pathological conditions, e.g. eye diseases such as AMD or DME, using the binding proteins of the invention.

The interaction of selected clones with dog VEGF-A164 (VEGF) and a negative control protein (MBP, *Escherichia coli* maltose binding protein) is shown by crude extract ELISA. The biotinylated dog VEGF-A164 and MBP were immobilized over NeutrAvidin. The numbers refer to single DARPin clones selected in ribosome display against dog VEGF-A164 or the corresponding human VEGF-A165.

A=Absorbance. Shaded bars indicate binding to dog VEGF-A164, black bars show non-specific background binding to MBP.

FIG. 2. Spheroid outgrowth inhibition by a selected DARPin.

The length of sprouts in a spheroid outgrowth inhibition assay are shown in presence of various concentrations of (a) DARPin #30 (amino acids 1 to 126 of SEQ ID NO:4), a DARPin with specificity to VEGF-Axxx, or (b) DARPin NC, a negative control DARPin with no specificity for VEGF-Axxx.

FIG. 3. Specific recognition of VEGF-A isoforms.

Surface Plasmon Resonance (SPR) analysis of binding proteins on VEGF-A isoforms.

(a) and (b): SPR analysis of AVASTIN® (bevacizumab). 250 nM of AVASTIN® (bevacizumab) was applied to a flow cell with immobilized dog VEGF-A164 (a) or dog VEGF-A164b (b) for 100 seconds, followed by washing with buffer flow.

(c) and (d): SPR analysis of DARPin #27 (amino acids 1 to 159 of SEQ ID NO:1). 250 nM of DARPin #27 was applied to a flow cell with immobilized dog VEGF-A164 (c) or dog VEGF-A164b (d) for 100 seconds, followed by washing with buffer flow.

RU=Resonance Units.

Figure 4:
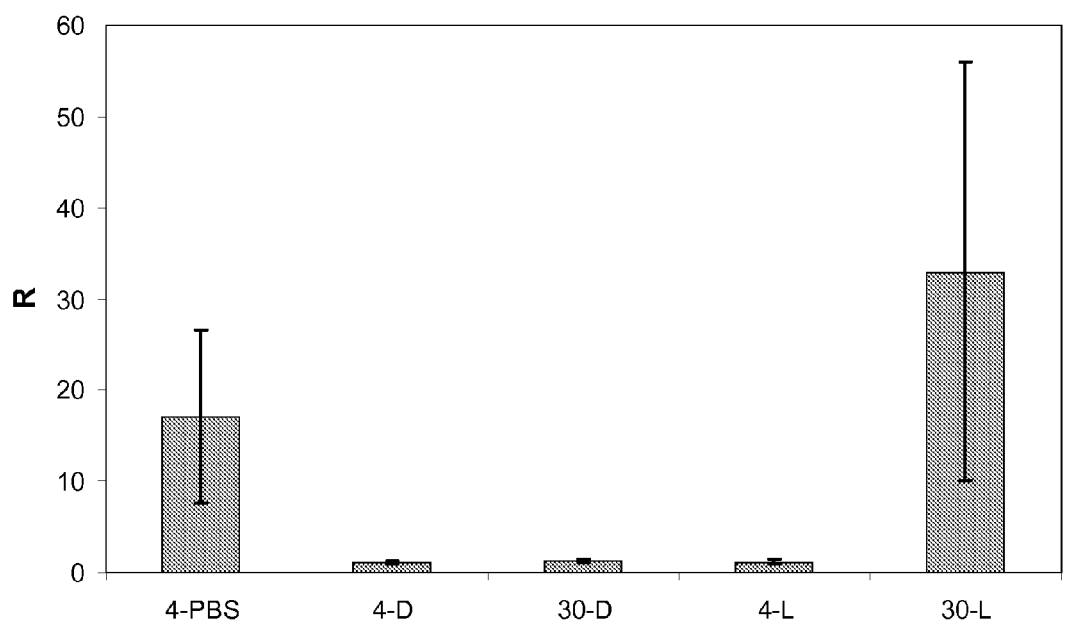

FIG. 4. Efficient inhibition of human VEGF-A165 in the rabbit eye.

Vascular leakage rabbit model to show the efficacy of a DARPin in inhibiting human VEGF-A165 in the eye in comparison to LUCENTIS® (ranibizumab). At day 1 either PBS, DARPin #30 or Lucentis® is applied by an intravitreal injection into one eye of each rabbit (treated eye). At day 4 or day 30 both eyes of each rabbit were challenged by intravitreal injection of 500 ng of human VEGF-A165. All eyes were evaluated 48 hours after the VEGF-A165 injection by measuring the fluorescein content in the vitreous and retina of all eyes one hour after intravenous injection of sodium fluorescein.

R=ratio of fluorescein measurements treated eye/untreated eye. Standard deviations are shown by an error bar. 4-PBS=ratio 4 days after injection of PBS (control); 4-D=ratio 4 days after injection of DARPin #30; 30-D=ratio 30 days after injection of DARPin #30; 4-L=ratio 4 days after injection of LUCENTIS® (ranibizumab); 30-L=ratio 30 days after injection of Lucentis®.

DETAILED DESCRIPTION OF THE INVENTION

Mammalian VEGF-A exists as two families of alternative spliced isoforms: (i) the pro-angiogenic "VEGF-Axxx" isoforms generated by proximal splicing of exon 8 and (ii) the anti-angiogenic "VEGF-Axxxb" isoforms generated by distal splicing of exon 8. Preferably, the binding domain according to the invention is specific for the pro-angiogenic VEGF-Axxx of dog, rabbit, monkey or human origin. More preferably, the binding domain according to the invention is specific for the pro-angiogenic VEGF-Axxx of human origin. Most preferred, the binding domain according to the invention is specific for human VEGF-A165.

The term "protein" refers to a polypeptide, wherein at least part of the polypeptide has, or is able to acquire a defined three-dimensional arrangement by forming secondary, tertiary, or quaternary structures within and/or between its polypeptide chain(s). If a protein comprises two or more polypeptides, the individual polypeptide chains may be linked non-covalently or covalently, e.g. by a disulfide bond between two polypeptides. A part of a protein, which individually has, or is able to acquire a defined three-dimensional arrangement by forming secondary or tertiary structures, is termed "protein domain". Such protein domains are well known to the practitioner skilled in the art.

The term "recombinant" as used in recombinant protein, recombinant protein domain and the like, means that said polypeptides are produced by the use of recombinant DNA technologies well known by the practitioner skilled in the relevant art. For example, a recombinant DNA molecule (e.g. produced by gene synthesis) encoding a polypeptide can be cloned into a bacterial expression plasmid (e.g. pQE30, Qiagen). When such a constructed recombinant expression plasmid is inserted into a bacteria (e.g. *E. coli*), this bacteria can produce the polypeptide encoded by this recombinant DNA. The correspondingly produced polypeptide is called a recombinant polypeptide.

The term "polypeptide tag" refers to an amino acid sequence attached to a polypeptide/protein, wherein said amino acid sequence is useful for the purification, detection, or targeting of said polypeptide/protein, or wherein said amino acid sequence improves the physicochemical behavior of the polypeptide/protein, or wherein said amino acid sequence possesses an effector function. The individual polypeptide tags, moieties and/or domains of a binding protein may be connected to each other directly or via polypeptide linkers. These polypeptide tags are all well known in the art and are fully available to the person skilled in the art. Examples of polypeptide tags are small polypeptide sequences, for example, His, myc, FLAG, or Strep-tags or moieties such as enzymes (for example enzymes like alkaline phosphatase), which allow the detection of said polypeptide/protein, or moieties which can be used for targeting (such as immunoglobulins or fragments thereof) and/or as effector molecules.

The term "polypeptide linker" refers to an amino acid sequence, which is able to link, for example, two protein domains, a polypeptide tag and a protein domain, a protein domain and a non-polypeptide moiety such as polyethylene glycol or two sequence tags. Such additional domains, tags, non-polypeptide moieties and linkers are known to the person skilled in the relevant art. A list of example is provided in the description of the patent application WO 02/20565. Particular examples of such linkers are glycine-serine-linkers and proline-threonine-linkers of variable lengths; preferably, said linkers have a length between 2 and 24 amino acids; more preferably, said linkers have a length between 2 and 16 amino acids.

In the context of the present invention, the term "polypeptide" relates to a molecule consisting of one or more chains of multiple, i.e. two or more, amino acids linked via peptide bonds. Preferably, a polypeptide consists of more than eight amino acids linked via peptide bonds.

The term "polymer moiety" refers to either a proteinaceous polymer moiety or a non-proteinaceous polymer moiety. A "proteinaceous polymer moiety" preferably is a polypeptide that does not form a stable tertiary structure while not forming more than 10% (preferably, not more than 5%; also preferred, not more than 2%; even more preferably, not more than 1%; and most preferably, no detectable amounts, as determined by size exclusion chromatography (SEC)) of oligomers or aggregates when stored at a concentration of about 0.1 mM in PBS at RT for one month. Such proteinaceous polymer moieties run at an apparent molecular weight in SEC that is higher than their effective molecular weight when using globular proteins as molecular weight standards for the SEC. Preferably, the apparent molecular weight of said proteinaceous polymer moieties determined by SEC is 1.5×, 2× or 2.5× higher than their effective molecular weight calculated from their amino acid sequence. Also preferably, the apparent molecular weights of said non-proteinaceous polymer moieties determined by SEC is 2×, 4× or 8× higher than their effective molecular weight calculated from their molecular composition. Preferably, more than 50%, 70% or even 90% of the amino acids of said proteinaceous polymer moiety do not form stable secondary structures at a concentration of about 0.1 mM in PBS at RT as determined by Circular Dichroism (CD) measurements. Most preferably, said proteinaceous polymer shows a typical near UV CD-spectra of a random coil conformation. Such CD analyses are well known to the person skilled in the art. Also preferable are proteinaceous polymer moieties that consist of more than 50, 100, 200, 300, 400, 500, 600, 700 or 800 amino acids. Examples of proteinaceous polymer moieties are XTEN® (a registered trademark of Amunix; WO 07/103,515) polypeptides, or polypeptides comprising proline, alanine and serine residues as described in WO 08/155,134. Such proteinaceous polymer moieties can be covalently attached to, for example, a binding domain of the invention by the generation of genetic fusion polypeptides using standard DNA cloning technologies, followed by their standard expression and purification. Examples of binding proteins comprising a repeat domain binding VEGF-Axxx and such a proteinaceous polymer moiety are shown in SEQ ID NO:1 and SEQ ID NO:4. The amino acid positions from 1 to 159 of SEQ ID NO:1 correspond to the repeat domain and the amino acid position 161 to 1'025 of SEQ ID NO:1 correspond to the proteinaceous polymer moiety. The amino acid positions from 1 to 126 of SEQ ID NO:4 correspond to the repeat domain and the amino acid positions 131 to 640 of SEQ ID NO:4 correspond to the proteinaceous polymer moiety.

A polymer moiety of the invention may vary widely in molecular weight (i.e. from about 1 kDa to about 150 kDa). Preferably, the polymer moiety has a molecular weight of at least 2, 5, 10, 20, 30, 50, 70 or 100 kDa.

Preferably, said polymer moiety is connected by a polypeptide linker to a binding domain. Examples of such polypeptide linkers are the amino acids 1 to 8 of SEQ ID NO:8 and SEQ ID NO:9.

Examples of non-proteinaceous polymer moieties are hydroxyethyl starch (HES), polyethylene glycol (PEG), polypropylene glycol, or polyoxyalkylene. The term "PEGylated" means that a PEG moiety is covalently attached to, for example, a polypeptide of the invention. Examples of repeat proteins containing a polypeptide linker between the repeat domain and a C-terminal Cys residue useful for binding a non-proteinaceous polymer moiety are SEQ ID NO:2, 3, 5, 6 and 7.

In a specific embodiment, a PEG moiety or any other non-proteinaceous polymer can, e.g., be coupled to a cysteine thiol via a maleimide linker with the cysteine being coupled via a peptide linker to the N- or C-terminus of a binding domain as described herein (e.g. SEQ ID NO:3).

The term "binding protein" refers to a protein comprising one or more binding domains and one or more polymer moieties as further explained below. Preferably, said binding protein comprises up to four binding domains. More preferably, said binding protein comprises up to two binding domains. Most preferably, said binding protein comprises only one binding domain. Furthermore, any such binding protein may comprise additional protein domains that are not binding domains, multimerization moieties, polypeptide tags, polypeptide linkers and/or a single Cys residue. Examples of multimerization moieties are immunoglobulin heavy chain constant regions which pair to provide functional immunoglobulin Fc domains, and leucine zippers or polypeptides comprising a free thiol which forms an intermolecular disulfide bond between two such polypeptides. The single Cys residue may be used for conjugating other moieties to the polypeptide, for example, by using the maleimide chemistry well known to the person skilled in the art.

Preferably, said binding protein comprises up to four polymer moieties. More preferably, said binding protein comprises up to two polymer moieties. Most preferably, said binding protein comprises only one polymer moiety.

Also preferably, said binding protein has an apparent molecular weight of at least 70, 100, 200, 300, 500 or 800 kDa when analyzed at a concentration of 0.1 mM in PBS at RT by SEC using globular proteins as molecular weight standards.

The term "binding domain" means a protein domain exhibiting the same "fold" (three-dimensional arrangement) as a protein scaffold and having a predetermined property, as defined below. Such a binding domain may be obtained by rational, or most commonly, combinatorial protein engineering techniques, skills which are known in the art (Skerra, 2000, loc. cit.; Binz et al., 2005, loc. cit.). For example, a binding domain having a predetermined property can be obtained by a method comprising the steps of (a) providing a diverse collection of protein domains exhibiting the same fold as a protein scaffold as defined further below; and (b) screening said diverse collection and/or selecting from said diverse collection to obtain at least one protein domain having said predetermined property. The diverse collection of protein domains may be provided by several methods in accordance with the screening and/or selection system being used, and may comprise the use of methods well known to the person skilled in the art, such as phage display or ribosome display.

The term "protein scaffold" means a protein with exposed surface areas in which amino acid insertions, substitutions or deletions are highly tolerable. Examples of protein scaffolds that can be used to generate binding domains of the present invention are antibodies or fragments thereof such as single-chain Fv or Fab fragments, protein A from *Staphylococcus aureus*, the bilin binding protein from *Pieris brassicae* or other lipocalins, ankyrin repeat proteins or other repeat proteins, and human fibronectin. Protein scaffolds are known to the person skilled in the art (Binz et al., 2005, loc. cit.; Binz et al., 2004, loc. cit.).

The term "predetermined property" refers to a property such as binding to a target, blocking of a target, activation of a target-mediated reaction, enzymatic activity, and related further properties. Depending on the type of desired property, one of ordinary skill will be able to identify format and necessary steps for performing screening and/or selection of a binding domain with the desired property. Preferably, said predetermined property is binding to a target.

Preferably, the binding protein of the invention is not an antibody or a fragment thereof, such as Fab or scFv fragments. Antibodies and fragments thereof are well known to the person skilled in the art.

Also preferably, the binding domain of the invention does not comprise an immunoglobulin fold as present in antibodies and/or the fibronectin type III domain. An immunoglobulin fold is a common all-β protein fold that consists of a 2-layer sandwich of about 7 anti-parallel β-strands arranged in two β-sheets. Immunoglobulin folds are well known to the person skilled in the art. For example, such binding domains comprising an immunoglobulin fold are described in WO 07/080,392 or WO 08/097,497.

Further preferably, the binding domain of the invention does not comprise an immunoglobulin-like domain as found in VEGFR-1 or VEGFR-2. Such binding domains are described in WO 00/075319.

A preferred binding domain is a binding domain having anti-angiogenic effects. The anti-angiogenic effect of a binding domain can be determined by assays well know to the person skilled in the art, such as the sprouting assay of HUVEC spheroids described in Example 2.

Further preferred is a binding domain comprising between 70 and 300 amino acids, in particular between 100 and 200 amino acids.

Further preferred is a binding domain devoid of a free Cys residue. A free Cys residue is not involved in the formation of a disulfide bond. Even more preferred is a binding domain free of any Cys residue.

A preferred binding domain of the invention is a repeat domain or a designed repeat domain, preferably as described in WO 02/20565.

A particularly preferred binding domain is a designed ankyrin repeat domain (Binz, H. K. et al., 2004, loc. cit.), preferably as described in WO 02/20565. Examples of designed ankyrin repeat domains are shown in the Examples.

The definitions hereinafter for repeat proteins are based on those in patent application WO 02/20565. Patent application WO 02/20565 further contains a general description of repeat protein features, techniques and applications.

The term "repeat proteins" refers to a protein comprising one or more repeat domains. Preferably, each of said repeat proteins comprises up to four repeat domains. More preferably, each of said repeat proteins comprises up to two repeat domains. Most preferably, each of the repeat proteins comprises only one repeat domain. Furthermore, said repeat protein may comprise additional non-repeat protein domains, polypeptide tags and/or polypeptide linkers.

The term "repeat domain" refers to a protein domain comprising two or more consecutive repeat units (modules) as structural units, wherein said structural units have the same fold, and stack tightly to create, for example, a superhelical structure having a joint hydrophobic core.

The term "designed repeat protein" and "designed repeat domain" refer to a repeat protein or repeat domain, respectively, obtained as the result of the inventive procedure explained in patent application WO 02/20565. Designed repeat proteins and designed repeat domains are synthetic and not from nature. They are man-made proteins or domains, respectively, obtained by expression of correspondingly designed nucleic acids. Preferably, the expression is done in eukaryotic or prokaryotic cells, such as bacterial cells, or by using a cell-free in vitro expression system.

The term "structural unit" refers to a locally ordered part of a polypeptide, formed by three-dimensional interactions between two or more segments of secondary structure that are near one another along the polypeptide chain. Such a structural unit exhibits a structural motif. The term "structural motif" refers to a three-dimensional arrangement of secondary structure elements present in at least one structural unit. Structural motifs are well known to the person skilled in the art. Structural units alone are not able to acquire a defined three-dimensional arrangement; however, their consecutive arrangement, for example as repeat modules in a repeat domain, leads to a mutual stabilization of neighboring units resulting in a superhelical structure.

The term "repeat unit" refers to amino acid sequences comprising repeat sequence motifs of one or more naturally occurring repeat proteins, wherein said "repeat units" are found in multiple copies, and which exhibit a defined folding topology common to all said motifs determining the fold of the protein. Examples of such repeat units are armadillo repeat units, leucine-rich repeat units, ankyrin repeat units, tetratricopeptide repeat units, HEAT repeat units, and leucine-rich variant repeat units. Naturally occurring proteins containing two or more such repeat units are referred to as "naturally occurring repeat proteins". The amino acid sequences of the individual repeat units of a repeat protein may have a significant number of mutations, substitutions, additions and/or deletions when compared to each other, while still substantially retaining the general pattern, or motif, of the repeat units.

Preferably, the repeat units used for the deduction of a repeat sequence motif are homologous repeat units obtained from repeat domains selected on a target, for example as described in Example 1 and having the same target-specificity.

The term "repeat sequence motif" refers to an amino acid sequence, which is deduced from one or more repeat units. Preferably, said repeat units are from repeat domains having binding specificity for the same target.

The term "folding topology" refers to the tertiary structure of said repeat units. The folding topology will be determined by stretches of amino acids forming at least parts of α-helices or β-sheets, or amino acid stretches forming linear polypeptides or loops, or any combination of α-helices, β-sheets and/or linear polypeptides/loops.

The term "consecutive" refers to an arrangement, wherein the repeat units or repeat modules are arranged in tandem. In designed repeat proteins, there are at least 2, usually about 2 to 6, in particular at least about 6, frequently 20 or more repeat units. In most cases, repeat units will exhibit a high degree of sequence identity (same amino acid residues at corresponding positions) or sequence similarity (amino acid residues being different, but having similar physicochemical properties), and some of the amino acid residues might be key residues being strongly conserved in the different repeat units found in naturally occurring proteins. However, a high degree of sequence variability by amino acid insertions and/or deletions, and/or substitutions between the different repeat units found in naturally occurring proteins will be possible as long as the common folding topology is maintained.

Methods for directly determining the folding topology of repeat proteins by physicochemical means such as X-ray crystallography, NMR or CD spectroscopy, are well known to the practitioner skilled in the art. Methods for identifying and determining repeat units or repeat sequence motifs or for identifying families of related proteins comprising such repeat units or motifs, such as homology searches (BLAST etc.), are well established in the field of bioinformatics, and are well known to the practitioner in the art. The step of refining an initial repeat sequence motif may comprise an iterative process.

The term "repeat modules" refers to the repeated amino acid sequences of the designed repeat domains, which are originally derived from the repeat units of naturally occurring repeat proteins. Each repeat module comprised in a repeat domain is derived from one or more repeat units of the family or subfamily of naturally occurring repeat proteins, e.g. the family of armadillo repeat proteins or ankyrin repeat proteins.

"Repeat modules" may comprise positions with amino acid residues present in all copies of corresponding repeat modules ("fixed positions") and positions with differing or "randomized" amino acid residues ("randomized positions").

The term "capping module" refers to a polypeptide fused to the N- or C-terminal repeat module of a repeat domain, wherein said capping module forms tight tertiary interactions with said repeat module thereby providing a cap that shields the hydrophobic core of said repeat module at the side not in contact with the consecutive repeat module from the solvent. Said N- and/or C-terminal capping module may be, or may be derived from, a capping unit or other domain found in a naturally occurring repeat protein adjacent to a repeat unit. The term "capping unit" refers to a naturally occurring folded polypeptide, wherein said polypeptide defines a particular structural unit which is N- or C-terminally fused to a repeat unit, wherein said polypeptide forms tight tertiary interactions with said repeat unit thereby providing a cap that shields the hydrophobic core of said repeat unit at one side from the solvent. Such capping units may have sequence similarities to said repeat sequence motif. Capping modules and capping repeats are described in WO 02/020565. For example, the N-terminal capping module of SEQ ID NO:2 is encoded by the amino acids from position 1 to 32. Also preferred is such an N-terminal capping module having a glycine or aspartate residue at position 5.

The term "target" refers to an individual molecule such as a nucleic acid molecule, a polypeptide or protein, a carbohydrate, or any other naturally occurring molecule, including any part of such individual molecule, or complexes of two or more of such molecules. The target may be a whole cell or a tissue sample, or it may be any non-natural molecule or moiety. Preferably, the target is a naturally occurring or non-natural polypeptide or a polypeptide containing chemical modifications, for example modified by natural or non-natural phosphorylation, acetylation, or methylation. In the particular application of the present invention, the target is VEGF-Axxx or VEGFR-2.

The term "consensus sequence" refers to an amino acid sequence, wherein said consensus sequence is obtained by structural and/or sequence aligning of multiple repeat units. Using two or more structural and/or sequence aligned repeat units, and allowing for gaps in the alignment, it is possible to determine the most frequent amino acid residue at each position. The consensus sequence is that sequence which comprises the amino acids which are most frequently represented at each position. In the event that two or more amino acids are represented above-average at a single position, the consensus sequence may include a subset of those amino acids. Said two or more repeat units may be taken from the repeat units comprised in a single repeat protein, or from two or more different repeat proteins.

Consensus sequences and methods to determine them are well known to the person skilled in the art.

A "consensus amino acid residue" is the amino acid found at a certain position in a consensus sequence. If two or more, e.g. three, four or five, amino acid residues are found with a similar probability in said two or more repeat units, the consensus amino acid may be one of the most frequently found amino acids or a combination of said two or more amino acid residues.

Further preferred are non-naturally occurring binding proteins or binding domains.

The term "non-naturally occurring" means synthetic or not from nature, more specifically, the term means made from the hand of man. The term "non-naturally occurring binding protein" or "non-naturally occurring binding domain" means that said binding protein or said binding domain is synthetic (i.e. produced by chemical synthesis from amino acids) or recombinant and not from nature. "Non-naturally occurring binding protein" or "non-naturally occurring binding domain" is a man-made protein or domain, respectively, obtained by expression of correspondingly designed nucleic acids. Preferably, the expression is done in eukaryotic or bacterial cells, or by using a cell-free in vitro expression system. Further, the term means that the sequence of said binding protein or said binding domain is not present as a non-artificial sequence entry in a sequence database, for example in GenBank, EMBL-Bank or Swiss-Prot. These databases and other similar sequence databases are well known to the person skilled in the art.

A binding domain can inhibit VEGF-Axxx binding to VEGFR-2 either by binding to VEGF-Axxx or by binding to VEGFR-2 in a way that the apparent dissociation constant ($K_d$) between VEGF-Axxx and VEGFR-2 is increased more than $10^2$-fold, preferably more than $10^3$-fold, more preferably more than $10^4$-fold, more preferably more than $10^5$-fold, and most preferably more than $10^6$-fold. Preferably, the $K_d$ for the interaction of the binding domain to either VEGF-Axxx or VEGFR-2 is below $10^{-7}$M, preferably below $10^{-8}$M, more preferably below $10^{-6}$M, more preferably below $10^{-10}$M, and most preferably below $10^{-11}$M. Methods, to determine dissociation constants of protein-protein interactions, such as surface plasmon resonance (SPR) based technologies, are well known to the person skilled in the art.

A preferred binding domain binds VEGF-Axxx. Even more preferred is a binding domain that binds human VEGF-A165.

The term "PBS" means a phosphate buffered water solution containing 137 mM NaCl, 10 mM phosphate and 2.7 mM KCl and having a pH of 7.4.

Preferred is a binding protein and/or binding domain that does not lose its native three-dimensional structure upon incubation in PBS containing 100 mM dithiothreitol (DTT) for 1 or 10 hours at 37° C.

In one particular embodiment the invention relates to a binding protein comprising a binding domain inhibiting VEGF-Axxx binding to VEGFR-2 and having the indicated or preferred midpoint denaturation temperature and non-aggregating properties as defined above, wherein said binding protein inhibits sprouting of HUVEC spheroids with an $IC_{50}$ value below 100 nM.

The term "HUVEC" means human umbilical vein endothelial cells, which can be isolated from normal human umbilical vein and which are responsive to VEGF-A stimulation. Assays to measure the sprouting of HUVEC spheroids, such as that described in Example 2, are well known to the person skilled in the art.

An $IC_{50}$ value is the concentration of a substance, such as a binding protein or binding domain, which is required for 50% inhibition in vitro of an experimental determined parameter, such as the sprouting of HUVEC spheroids. $IC_{50}$ values can be readily determined by the person skilled in the art (Korff T. and Augustin H. G., J. Cell Biol. 143(5), 1341-52, 1998).

Preferred is a binding protein and/or binding domain that inhibits the sprouting of HUVEC spheroid with an $IC_{50}$ value below 10 nM, preferably below 1 nM, more preferably below 0.1 nM, and most preferably below 0.05 nM.

Further preferred is a monomeric binding protein and/or binding domain that inhibits the sprouting of HUVEC spheroids with an $IC_{50}$ value lower than the corresponding $IC_{50}$ value of ranibizumab (LUCENTIS®, a registered trademark of Genentech), bevacizumab (AVASTIN®, a registered trademark of Genentech), aflibercept (VEGF TRAP, a registered trademark of Regeneron), or pegaptanib (MACUGEN®, a registered trademark of Pfizer).

The $K_d$ for the interaction of a preferred binding domain to VEGF-B, VEGF-C, VEGF-D, PlGF or PDGF is above 1 nM, preferably above 10 nM, more preferably above $10^2$ nM, even more preferably above $10^3$ nM, and most preferably above $10^4$ nM.

Preferably, VEGF-Axxx is either dog VEGF-A164 or simian VEGF-A165 or human VEGF-A165, and VEGF-Axxxb is either dog VEGF-A164b or simian VEGF-A165b or human VEGF-A165b.

Another preferred embodiment is a recombinant binding protein comprising a binding domain, wherein said binding domain inhibits VEGF-Axxx binding to VEGFR-2 and wherein said binding domain is a repeat domain or a designed repeat domain. Such a repeat domain may comprise one, two, three or more internal repeat modules that will participate in binding to VEGF-Axxx. Preferably, such a repeat domain comprises an N-terminal capping module, two to four internal repeat modules, and a C-terminal capping module. Preferably, said binding domain is an ankyrin repeat domain or designed ankyrin repeat domain.

A preferred recombinant binding protein comprises a binding domain as described herein, conjugated to a polyethylene glycol (PEG) moiety, preferably wherein said PEG moiety is coupled to a single Cys residue of said binding domain. Preferably, said Cys residue is genetically introduced at the C-terminal end of said binding domain. The PEG moiety can then be coupled by chemical means, for example, by using maleimide chemistry well known to the person skilled in the art. Examples of such binding proteins comprising a PEG moiety conjugated to a single Cys residue are given in the Examples.

A preferred embodiment of the invention comprises a recombinant binding protein comprising a binding domain as described herein, wherein said binding domain is conjugated at its C-terminus via a peptide bond to SEQ ID NO:8, which is in turn conjugated at the C-terminal cysteine thiol to a maleimide-coupled PEG, such as α-[3-(3-maleimido-1-oxopropyl)amino]propyl-ω-methoxy-polyoxyethylene (NOF, Sunbright ME-200MA (20 kD) or Sunbright ME-400MA (40 kD)). In one embodiment the α-[3-(3-maleimido-1-oxopropyl)amino]propyl-ω-methoxy-polyoxyethylene has a molecular weight of at least about 2, 5, 10, 20, 30, 40, 50, 70, or 100 kD. In certain embodiments the α-[3-(3-maleimido-1-oxopropyl)amino]propyl-ω-methoxy-polyoxyethylene has a molecular weight of at least about 20 or at least about 40 kD.

Another preferred embodiment is a recombinant binding protein as defined above comprising at least one repeat domain with binding specificity for VEGF-Axxx, wherein said repeat domain competes for binding to VEGF-Axxx with a repeat domain selected from the group of the repeat domains of SEQ ID NO:1 to 7. Preferably, said repeat domain competes for binding to VEGF-Axxx with the repeat domain of SEQ ID NO:1 or 3. More preferably, said repeat domain competes for binding to VEGF-Axxx with the repeat domain of SEQ ID NO:3.

The term "compete for binding" means the inability of two different binding domains of the invention to bind simultaneously to the same target, while both are able to bind the same target individually. Thus, such two binding domains compete for binding to said target. Methods, such as competition ELISA or competition SPR measurements (e.g. by using the Proteon instrument from BioRad), to determine if two binding domains compete for binding to a target are well known to the practitioner in the art.

A recombinant binding protein that competes for binding to VEGF-Axxx with a selected repeat protein can be identified by methods well know to the person skilled in the art, such as a competition Enzyme-Linked ImmunoSorbent Assay (ELISA).

Another preferred embodiment is a recombinant binding protein comprising a repeat domain with binding specificity for VEGF-Axxx selected from the group consisting of the repeat domains of SEQ ID NO:1 to 7. Preferably, said repeat domain is selected from the repeat domains of SEQ ID NO:2 or 3. More preferably, said repeat domain is the repeat domain of SEQ ID NO:3.

One or more polyethylene glycol moieties may be attached at different positions in the binding protein, and such attachment may be achieved by reaction with amines, thiols or other suitable reactive groups. Attachment of polyethylene glycol moieties (PEGylation) may be site-directed, wherein a suitable reactive group is introduced into the protein to create a site where PEGylation preferentially occurs, or is originally present in the binding protein. The thiol group may be present in a cysteine residue; and the amine group may be, for example, a primary amine found at the N-terminus of the polypeptide or an amine group present in the side chain of an amino acid, such as lysine or arginine. In a preferred embodiment, the binding protein is modified so as to have a cysteine residue at a desired position, permitting site directed PEGylation on the cysteine, for example by reaction with a polyethylene glycol derivative carrying a maleimide function. The polyethylene glycol moiety may vary widely in molecular weight (i.e. from about 1 kDa to about 100 kDa) and may be branched or linear. Preferably, the polyethylene glycol has a molecular weight of about 1 to about 50 kDa, preferably about 10 to about 40 kDa, even more preferably about 15 to about 30 kDa, and most preferably about 20 kDa.

In a further embodiment, the invention relates to nucleic acid molecules encoding the particular recombinant binding proteins. Further, a vector comprising said nucleic acid molecule is considered.

Further, a pharmaceutical composition comprising one or more of the above mentioned binding proteins, in particular recombinant binding proteins comprising repeat domains, or nucleic acid molecules encoding the particular recombinant binding proteins, and optionally a pharmaceutical acceptable carrier and/or diluent is considered. Pharmaceutical acceptable carriers and/or diluents are known to the person skilled in the art and are explained in more detail below. Even further, a diagnostic composition comprising one or more of the above mentioned recombinant binding proteins, in particular binding proteins comprising repeat domains, is considered.

The binding protein of the invention suppresses or prevents VEGF induced pathological angiogenesis, vascular leakage (edema), pulmonary hypertension, tumor formation and/or inflammatory disorders. With "suppression" it is understood that the recombinant protein prevents the mentioned pathologies to some extent, e.g. to 10% or 20%, more preferably 50%, in particular 70%, 80% or 90%, or even 95%.

The term "edema" means a condition that is caused by vascular leakage. Vasodilation and increased permeability during inflammation can be predominant pathogenetic mechanisms. For instance, edema contributes to infarct expansion after stroke and may cause life-threatening intracranial hypertension in cancer patients. Further, extravasation of plasma proteins favors metastatic spread of occult tumors, and airway congestion may cause fatal asthmatic attacks. The increased vascular leakage which occurs during inflammation can lead to respiratory distress, ascites, peritoneal sclerosis (in dialysis patients), adhesion formation (abdominal surgery) and metastatic spreading.

The term "angiogenesis" means a fundamental process by which new blood vessels are formed. The primary angiogenic period in humans takes place during the first three months of embryonic development but angiogenesis also occurs as a normal physiological process during periods of tissue growth, such as an increase in muscle or fat and during the menstrual cycle and pregnancy.

The term "pathological angiogenesis" refers to the formation and growth of blood vessels during the maintenance and the progression of several disease states. Particular examples of pathological angiogenesis are found in blood vessels (atherosclerosis, hemangioma, hemangioendothelioma), bone and joints (rheumatoid arthritis, synovitis, bone and cartilage destruction, osteomyelitis, pannus growth, osteophyte formation, neoplasms and metastasis), skin (warts, pyogenic granulomas, hair growth, Kaposi's sarcoma, scar keloids, allergic edema, neoplasms), liver, kidney, lung, ear and other epithelia (inflammatory and infectious processes including hepatitis, glomerulonephritis, pneumonia; and asthma, nasal polyps, otitis, transplantation disorders, liver regeneration disorders, neoplasms and metastasis), uterus, ovary and placenta (dysfunctional uterine bleeding due to intra-uterine contraceptive devices, follicular cyst formation, ovarian hyperstimulation syndrome, endometriosis, neoplasms), brain, nerves and eye (retinopathy of prematurity, diabetic retinopathy, choroidal and other intraocular disorders, leukomalacia, neoplasms and metastasis), heart and skeletal muscle due to work overload, adipose tissue (obesity), endocrine organs (thyroiditis, thyroid enlargement, pancreas transplantation disorders), hematopoiesis (Kaposi syndrome in AIDS), hematologic malignancies (leukemias), and lymph vessels (tumor metastasis, lymphoproliferative disorders).

The term "retinal ischemic diseases" means that the retina's supply of blood and oxygen is decreased, the peripheral portions of the retina lose their source of nutrition and stop functioning properly. A particular example of a retinal ischemic disease is retinopathy. Common diseases which lead to retinopathy are diabetic retinopathy, central retinal vein occlusion, stenosis of the carotid artery, and sickle cell retinopathy. Diabetic retinopathy is a major cause of visual loss in diabetic patients. In the ischemic retina the growth of new blood vessels occurs (neovascularisation). These vessels often grow on the surface of the retina, at the optic nerve, or in the front of the eye on the iris. The new vessels cannot replace the flow of necessary nutrients and, instead, can cause many problems such as vitreous hemorrhage, retinal detachment, and uncontrolled glaucoma. These problems occur because new vessels are fragile and are prone to bleed. If caught in its early stages, proliferative diabetic retinopathy can sometimes be arrested with panretinal photocoagulation. However, in some cases, vitrectomy surgery is the only option.

Beside these retinopathies, vascular diseases of the eye also include ocular neovascularization diseases, such as macular degeneration and diabetic macular edema (DME). Macular degeneration results from the neovascular growth of the choroid vessel underneath the macula. There are two types of macular degeneration: dry and wet. While wet macular degeneration only comprises 15% of all macular degeneration, nearly all wet macular degeneration leads to blindness. In addition, wet macular degeneration nearly always results from dry macular degeneration. Once one eye is affected by wet macular degeneration, the condition almost always affects the other eye. Wet macular degeneration is often called age-related wet macular degeneration of wet-AMD as it is mostly found in elderly persons.

Diabetic retinopathy (DR) and DME are leading causes of blindness in the working-age population of most developed countries. The increasing number of individuals with diabetes worldwide suggests that DR and DME will continue to be major contributors to vision loss and associated functional impairment for years to come. Several biochemical mechanisms, including protein kinase C-β activation, increased vascular endothelial growth factor production, oxidative stress, and accumulation of intracellular sorbitol and advanced glycosylation end products, may contribute to the vascular disruptions that characterize DR/DME. The inhibition of these pathways holds the promise of intervention for DR and DME.

The term "pulmonary hypertension" means a disorder in which the blood pressure in the pulmonary arteries is abnormally high. In the absence of other diseases of the heart or lungs it is called primary pulmonary hypertension. Diffuse narrowing of the pulmonary arterioles occurs as a result of pathological arteriogenesis followed by pulmonary hypertension as a response to the increased resistance to blood flow. The incidence is 8 out of 100'000 people. However, pulmonary hypertension can also occur as a complication of Chronic Obstructive Pulmonary Diseases (COPD) such as emphysema, chronic bronchitis or diffuse interstitial fibrosis and in patients with asthmatiform COPD. The incidence of COPD is approximately 5 out of 10'000 people.

Furthermore the binding proteins of the invention can be used to treat inflammation and more specifically inflammatory disorders.

The term "inflammation" as used herein means, the local reaction to injury of living tissues, especially the local reaction of the small blood vessels, their contents, and their associated structures. The passage of blood constituents through the vessel walls into the tissues is the hallmark of inflammation, and the tissue collection so formed is termed the exudates or edema. Any noxious process that damages living tissue, e.g. infection with bacteria, excessive heat, cold, mechanical injury such as crushing, acids, alkalis, irradiation, or infection with viruses can cause inflammation irrespective of the organ or tissue involved. It should be clear that diseases classified as "inflammatory diseases" and tissue reactions ranging from burns to pneumonia, leprosy, tuberculosis, and rheumatoid arthritis are all "inflammations".

The binding proteins according to the invention can be used to treat tumor formation. The term "tumor" means a mass of abnormal tissue that arises without obvious cause from pre-existing body cells, has no purposeful function, and is characterized by a tendency to autonomous and unrestrained growth. Tumors are quite different from inflammatory or other swellings because the cells in tumors are abnormal in their appearance and other characteristics. Abnormal cells, i.e. the kind of cells that generally make up tumors, differ from normal cells in having undergone one or more of the following alterations:
(1) hypertrophy, or an increase in the size of individual cells;
(2) hyperplasia or an increase in the number of cells within a given zone; (3) anaplasia, or a regression of the physical characteristics of a cell toward a more primitive or undifferentiated type. Tumors may be benign, for example lipomas, angiomas, osteomas, chondromas, and adenomas. Examples of malignant tumors are carcinomas (such as the breast tumors, carcinomas in the respiratory and gastrointestinal tracts, the endocrine glands, and the genitourinary system), sarcomas (in connective tissues, including fibrous tissues, adipose (fat) tissues, muscle, blood vessels, bone, and cartilage), carcinosarcoma (in both epithelial and connective tissue) leukemias and lymphomas, tumors of nerve tissues (including the brain), and melanoma (a cancer of the pigmented skin cells). The use of the binding proteins of the present invention against tumors can also be in combination with any other tumor therapy known in the art such as irradiation, photo-dynamic therapy, chemotherapy or surgery.

A pharmaceutical composition comprises binding proteins as described above and a pharmaceutically acceptable carrier, excipient or stabilizer (Remington's Pharmaceutical Sciences 16th edition, Osol, A. Ed. [1980]). Suitable carriers, excipients or stabilizers known to the skilled man are saline, Ringer's solution, dextrose solution, Hank's solution, fixed oils, ethyl oleate, 5% dextrose in saline, substances that enhance isotonicity and chemical stability, buffers and preservatives. Other suitable carriers include any carrier that does not itself induce the production of antibodies harmful to the individual receiving the composition such as proteins, polysaccharides, polylactic acids, polyglycolic acids, polymeric amino acids and amino acid copolymers. A pharmaceutical composition may also be a combination formulation, comprising an additional active agent, such as an anti-cancer agent or an anti-angiogenic agent (for example human VEGF-Axxxb; preferably, human VEGF-A165b).

A preferred pharmaceutical composition for the treatment of eye diseases comprises binding proteins as described above and a detergent such as nonionic detergent, including but not limited to polysorbate 20 (e.g. about 0.04%), a buffer such as histidine, phosphate or lactic acid and a sugar such as sucrose or trehalose. Preferably, such a composition comprises binding proteins as described above and PBS. Said or any other pharmaceutical compositions described herein may be administered locally, either topically to a portion of the eye or be injected into the eye for instance into the subconjunctivital, peri- or retrobulbar space or directly into the eye. Alternatively, said or such other pharmaceutical compositions may be administered systemically by parental administration. Preferably, said or such other pharmaceutical composition is applied to the eye by an intravitreous injection. Also preferably, said pharmaceutical composition is applied to the eye topically and as an eye drop. The eye drop may be applied to the cornea (clear part in the centre of the eye) thereby allowing the molecules to permeate into the eye. For the treatment of a disease affecting the posterior of the eye, it may be most desirable that the binding protein penetrates the sclera when injected under the conjunctiva or around the globe. The administering of the binding protein may be performed after a preliminary step of modulating the surface of the eye to improve penetration of the molecules. Preferably, the epithelial layer such as the corneal epithelium is modulated by a penetration enhancer to allow for a sufficient and rapid penetration of the molecules as for example described above. The use of the binding proteins of the present invention against eye diseases can also be in combination with any other therapy known in the art such as photo-dynamic therapy.

The formulations to be used for in vivo administration must be aseptic or sterile. This is readily accomplished by filtration through sterile filtration membranes.

Sustained-release preparations may be prepared. In one embodiment of the invention, an intraocular implant can be used for providing the binding protein of the invention. Suitable examples of sustained-release preparations include semipermeable matrices of solid hydrophobic polymers containing a polypeptide of the invention, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides, copolymers of L-glutamic acid and gamma-ethyl-L-glutamate, non-degradable ethylene-vinyl acetate, degradable lactic acid-glycolic acid copolymers such as the LUPRON DEPOT® (injectable microspheres composed of lactic acid-glycolic acid copolymer and leuprolide acetate), and poly-D-(−)-3-hydroxybutyric acid.

The pharmaceutical composition may be administered by any suitable method within the knowledge of the skilled man. The preferred route of administration is parenterally. In parental administration, the medicament of this invention will be formulated in a unit dosage injectable form such as a solution, suspension or emulsion, in association with the pharmaceutically acceptable excipients as defined above. The dosage and mode of administration will depend on the individual to be treated and the particular disease. Generally, the pharmaceutical composition is administered so that the binding protein of the present invention is given at a dose between 1 µg/kg and 20 mg/kg, more preferably between 10 µg/kg and 5 mg/kg, most preferably between 0.1 and 2 mg/kg. Preferably, it is given as a bolus dose. Continuous infusion may also be used and includes continuous subcutaneous delivery via an osmotic minipump. If so, the pharmaceutical composition may be infused at a dose between 5 and 20 µg/kg/minute, more preferably between 7 and 15 µg/kg/minute. In particular, the pharmaceutical composition is administered by injections into the eye so that the binding protein of the invention is given at a dose between 0.1 mg and 10 mg per injection, more preferably between 0.3 and 6 mg per injection, most preferably between 1 mg and 4 mg per injection. Further, the pharmaceutical composition is administered by eye drops to the eye so that a single drop of a solution containing a concentration of the binding protein of the invention between 10 and 120 mg/ml, more preferably between 20 and 100 mg/ml, most preferably between 40 and 80 mg/ml is applied to the eye.

In another embodiment of the invention a binding protein inhibiting the activity of VEGF-Axxx, as described above, can be used in combination with a binding protein or small molecule inhibiting the activity of PIGF, with the same inhibition levels of PIGF as described above for VEGF-Axxx. This embodiment is based on the fact that PIGF is found to be angiogenic at sites where VEGF-Axxx levels are increased. Further, a binding protein inhibiting the activity of VEGF-Axxx, as described above, can be used in combination with a binding protein or small molecule inhibiting the activity of platelet-derived growth factor (PDGF), VEGF-C or other members of the VEGF family of proteins, tumor necrosis factor alpha (TNFalpha), delta-ligand like 4 (Dll4), interleukin 6 (IL-6), neuropilin or angiopoietin 2 (Ang2).

The invention further provides methods of treatment. In one aspect, a method of treating a retinopathy is provided, the method comprising administering, to a patient in need thereof, a therapeutically effective amount of a binding protein of the invention, in particular a binding protein that inhibits the interaction between human VEGF-Axxx and human VEGFR-2, but not the interaction between human VEGF-Axxxb and human VEGFR-2, and the binding protein inhibits VEGFR-2 mediated angiogenesis.

The invention further relates to methods for using a binding protein as described to inhibit a VEGF-A biological activity in a cell or to inhibit a biological activity mediated by VEGFR-2. The cell may be situated in vivo or ex vivo, and may be, for example, a cell of a living organism, a cultured cell or a cell in a tissue sample. The method may comprise contacting said cell with any of the VEGF-A/VEGFR-2 interaction inhibiting binding proteins disclosed herein, in an amount and for a time sufficient to inhibit such biological activity.

The invention provides a method for treating a subject having a condition which responds to the inhibition of VEGF-Axxx or VEGFR-2. Such a method comprises administering to said subject an effective amount of a binding protein described herein. A condition may be one that is characterized by inappropriate angiogenesis. A condition may be a hyperproliferative condition. Examples of conditions (or disorders) suitable for treatment include autoimmune disorders, inflammatory disorders, retinopathies (particularly proliferative retinopathies), and cancers, in particular one of the diseases described above. Any of the binding proteins described herein may be used for the preparation of a medicament for the treatment of such a disorder, particularly a disorder selected from the group consisting of: an autoimmune disorder, an inflammatory disorder, a retinopathy, and a cancer. Preferred conditions (or disorders) suitable for treatment are first-line metastatic renal cell carcinoma, relapsed glioblastoma multiforme, adjuvant colon cancer, adjuvant HER2-negative breast cancer, adjuvant HER2-positive breast cancer, adjuvant non-small cell lung cancer, diffuse large B-cell lymphoma, first-line advanced gastric cancer, first-line HER2-negative metastatic breast cancer, first-line HER2-positive metastatic breast cancer, first-line metastatic ovarian cancer, gastrointestinal stromal tumors, high risk carcinoid, hormone refractory prostate cancer, newly diagnosed glioblastoma multiforme, metastatic head and neck cancer, relapsed platinum-sensitive ovarian cancer, second-line metastatic breast cancer, extensive small cell lung cancer, non-squamous, non-small cell lung cancer with previously treated CNS metastases and relapsed multiple myeloma, prostate cancer, non-small cell lung cancer (NSCLC), colorectal cancer and pancreatic cancer, advanced ovarian cancer (AOC), AOC patients with symptomatic malignant ascites and non-Hodgkin's lymphoma.

The recombinant binding protein according to the invention may be obtained and/or further evolved by several methods such as display on the surface of bacteriophages (WO 90/02809, WO 07/006,665) or bacterial cells (WO 93/10214), ribosomal display (WO 98/48008), display on plasmids (WO 93/08278) or by using covalent RNA-repeat protein hybrid constructs (WO 00/32823), or intracellular expression and selection/screening such as by protein complementation assay (WO 98/341120). Such methods are known to the person skilled in the art.

A library of ankyrin repeat proteins used for the selection/screening of a recombinant binding protein according to the invention may be obtained according to protocols known to the person skilled in the art (WO 02/020565, Binz, H. K. et al., JMB, 332, 489-503, 2003, and Binz et al., 2004, loc. cit). The use of such a library for the selection VEGF-Axxx specific DARPins is given in Example 1. In analogy, the ankyrin repeat sequence motifs as presented above can used to build libraries of ankyrin repeat proteins that may be used for the selection or screening of VEGF-Axxx specific DARPins. Furthermore, repeat domains of the present invention may be modularly assembled from repeat modules according the current inventions and appropriate capping modules (Forrer, P., et al., FEBS letters 539, 2-6, 2003) using standard recombinant DNA technologies (e.g. WO 02/020565, Binz et al., 2003, loc. cit. and Binz et al., 2004, loc. cit).

The invention is not restricted to the particular embodiments described in the Examples. Other sources may be used and processed following the general outline described below.

EXAMPLES

All of the starting materials and reagents disclosed below are known to those skilled in the art, and are available commercially or can be prepared using well-known techniques.

Materials

Chemicals were purchased from Fluka (Switzerland). Oligonucleotides were from Microsynth (Switzerland). Unless stated otherwise, DNA polymerases, restriction enzymes and buffers were from New England Biolabs (USA) or Fermentas (Lithuania). The cloning and protein production strain was *E. coli* XL1-blue (Stratagene, USA). VEGF variants were from R&D Systems (Minneapolis, USA) or were produced in Chinese Hamster Ovary Cells or in *Pichia pastoris* and purified according to standard protocols (Rennel, E. S. et al., European J. Cancer 44, 1883-94, 2008; *Pichia* expression system from Invitrogen). Biotinylated VEGF variants were obtained chemically via coupling of the biotin moiety to primary amines of the purified VEGF variants using standard biotinylation reagents and methods (Pierce, USA).

Molecular Biology

Unless stated otherwise, methods are performed according to described protocols (Sambrook J., Fritsch E. F. and Maniatis T., Molecular Cloning: A Laboratory Manual, Cold Spring Harbor Laboratory 1989, New York).

Designed Ankyrin Repeat Protein Libraries

The N2C and N3C designed ankyrin repeat protein libraries are described (WO 02/20565; Binz et al. 2003, loc. cit.; Binz et al. 2004, loc. cit.). The digit in N2C and N3C describes the number of randomized repeat modules present between the N-terminal and C-terminal capping modules. The nomenclature used to define the positions inside the repeat units and modules is based on Binz et al. 2004, loc. cit. with the modification that borders of the repeat modules and repeat units are shifted by one amino acid position. For example, position 1 of a repeat module of Binz et al. 2004 (loc. cit.) corresponds to position 2 of a repeat module of the current disclosure and consequently position 33 of a repeat module of Binz et al. 2004, loc. cit. corresponds to position 1 of a following repeat module of the current disclosure.

All the DNA sequences were confirmed by sequencing, and the calculated molecular weight of all described proteins was confirmed by mass spectrometry.

Example 1

Selection of Binding Proteins Comprising a Repeat Domain with Binding Specificity for VEGF-Axxx Using ribosome display (Hanes, J. and Plückthun, A., PNAS 94, 4937-42, 1997) many designed ankyrin repeat proteins (DARPins) with binding specificity for VEGF-Axxx were selected from the N2C or N3C DARPin libraries described by Binz et al. 2004 (loc. cit.). The binding of the selected clones toward specific (VEGF-Axxx) and unspecific (MBP, *E. coli* maltose binding protein) targets was assessed by crude extract ELISA indicating that VEGF-Axxx binding proteins were successfully selected (FIG. 1). The repeat domains of SEQ ID NO:1 to 7 constitute amino acid sequences of selected binding proteins comprising a repeat domain with binding specificity for VEGF-Axxx. Sequence analysis of selected binders revealed specific ankyrin repeat sequence motifs inherent to certain selected families of binders.

Selection of VEGF-Axxx Specific Ankyrin Repeat Proteins by Ribosome Display

The selection of VEGF-Axxx specific ankyrin repeat proteins was performed by ribosome display (Hanes and Plückthun, loc. cit.) using dog VEGF-A164 or human VEGF-A165 as target proteins, the library of designed ankyrin repeat proteins as described (WO 02/020565, Binz et al., 2003, loc. cit. and Binz et al., 2004, loc. cit) and established protocols (Zahnd, C., Amstutz, P. and Plückthun, A., Nat. Methods 4, 69-79, 2007). Ribosome-display selection rounds were performed on dog or human VEGF variants (including biotinylated variants immobilized over neutravidin or streptavidin) with both the N2C and N3C DARPin libraries using established protocols (Binz et al. 2004, loc. cit.). The number of reverse transcription (RT)-PCR cycles after each selection round was constantly reduced from 40 to 30, adjusting to the yield due to enrichment of binders. Four initial selection rounds on dog VEGF yielded pools of nanomolar-affinity DARPins, as revealed by ELISA and SPR measurements of single clones. To find DARPins with further improved affinities, additional off-rate selections were performed on biotinylated human or dog VEGF immobilized over neutravidin or streptavidin, taking pools after the second and third initial ribosome-display selection rounds, followed by an on-rate selection round on human VEGF.

Selected Clones Bind Specifically to VEGF-Axxx as Shown by Crude Extract ELISA

Individual selected DARPins specifically binding VEGF-Axxx were identified by an enzyme-linked immunosorbent assay (ELISA) using crude *Escherichia coli* extracts of DARPin expression cells using standard protocols. Selected clones were cloned into the pQE30 (Qiagen) expression vector, transformed into *E. coli* XL1-Blue (Stratagene) and then grown overnight at 37° C. in a 96-deep-well plate (each clone in a single well) containing 1 ml growth medium (2YT containing 1% glucose and 100 μg/ml ampicillin). 1 ml of fresh 2YT containing 50 μg/ml ampicillin was inoculated with 100 μl of the overnight culture in a fresh 96-deep-well plate. After incubation for 2 h at 37° C., expression was induced with IPTG (1 mM final concentration) and continued for 3 h. Cells were harvested, resuspended in 100 μl B-PERII (Pierce) and incubated for 15 min at room temperature with shaking. Then, 900 μl PBS-TB (PBS supplemented with 0.2% BSA, 0.1% Tween 20, pH 7.4) were added and cell debris were removed by centrifugation. 100 μl of each lysed clone were applied to a well of a NeutrAvidin coated MaxiSorp plate containing either a VEGF-Axxx variant or the unrelated MBP immobilized via their biotin moiety and incubated for 1 h at RT. After extensive washing with PBS-T (PBS supplemented with 0.1% Tween 20, pH 7.4) the plate was developed using standard ELISA procedures using the monoclonal anti-RGS $(His)_4$ antibody (34650, Qiagen) as primary antibody and a polyclonal goat anti-mouse antibody conjugated with alkaline phosphatase (A3562, Sigma) as secondary reagent. Binding was then detected by using disodium 4-nitrophenyl phosphate (4NPP, Fluka) as a substrate for alkaline phosphatase. The color development was measured at 405 nm. The results from an example crude extract ELISA used to identify DARPins binding to VEGF-Axxx is shown in FIG. 1. Screening of several hundred clones by such a crude cell extract ELISA revealed more than hundred different DARPins with specificity for VEGF-Axxx. These binding proteins were chosen for further analysis. Examples of amino acid sequences of selected ankyrin repeat domains that specifically bind to VEGF-Axxx are provided in SEQ ID NO:1 to 7.

Deducing Repeat Sequence Motives from Selected Repeat Domains with Binding Specificity for VEGF-Axxx The amino acid sequences of selected repeat domains with binding specificity for VEGF-Axxx were further analyzed by sequence analyzing tools known to the practitioner in the art (WO 02/020565; Forrer et al., 2003, loc. cit.; Forrer, P., Binz, H. K., Stumpp, M. T. and Plückthun, A., ChemBioChem, 5(2), 183-189, 2004). Nevertheless, in contrast to WO 02/020565 where naturally occurring repeat motifs were used to deduce repeat sequence motifs, here the repeat sequence motifs were deduced from the repeat units of selected repeat domains with binding specificity for VEGF-Axxx. Thereby families of selected repeat domains comprising a common repeat sequence motif were determined.

High Level and Soluble Expression of DARPins

For further analysis, the selected clones showing specific VEGF-Axxx binding in the crude cell extract ELISA as described above were expressed in *E. coli* XL1-blue cells and purified using their His-tag using standard protocols. 25 ml of stationary overnight cultures (LB, 1% glucose, 100 mg/l of ampicillin; 37° C.) were used to inoculate 1 l cultures (same medium). At A(600)=0.7, the cultures were induced with 0.5 mM IPTG and incubated at 37° C. for 4 h. The cultures were centrifuged and the resulting pellets were resuspended in 40 ml of TBS500 (50 mM Tris-HCl, 500 mM NaCl, pH 8) and sonicated. The lysate was recentrifuged, and glycerol (10% (v/v) final concentration) and imidazole (20 mM final concentration) were added to the resulting supernatant. Proteins were purified over a Ni-nitrilotriacetic acid column (2.5 ml column volume) according to the manufacturer's instructions (QIAgen, Germany). Up to 200 mg of highly soluble DARPins with binding specificity to VEGF-Axxx could be purified from one liter of *E. coli* culture with a purity >95% as estimated from SDS-15% PAGE. Such purified DARPins are used for further characterizations.

Example 2

Determination of IC$_{50}$ Values of Selected DARPins with Binding Specificity to VEGF-Axxx in a Spheroid Outgrowth Assay Addition of VEGF-Axxx to HUVEC spheroids embedded in collagen matrices leads to spheroid sprouting. Addition of an inhibitor of VEGF-Axxx will block sprout formation, which can be quantified statistically by the numbers and lengths of sprouts. By adding different concentration of inhibitor and a constant amount of VEGF, the IC$_{50}$ can be determined.

Inhibition of Spheroid Sprouting by VEGF-Axxx Specific DARPins

Spheroid outgrowth assays were done according to standard protocols (Korff et al., loc. cit.). DARPins with specificity for VEGF-Axxx were selected and purified to >96% purity as described in Example 1. Human umbilical vein cells were grown to confluency in monolayer culture. After trypsinization, the cell suspension was placed in a hanging drop to form spheroids, i.e. approximately 500 organized aggregated HUVECs. Spheroids were embedded in a collagen matrix and stimulated with VEGF-A165 to initiate sprout outgrowth. Sprouting inhibitors were added additionally to observe their effects on sprouting inhibition. Sprout numbers per spheroid and sprout lengths were quantified using a graphical software.

Figure 1:
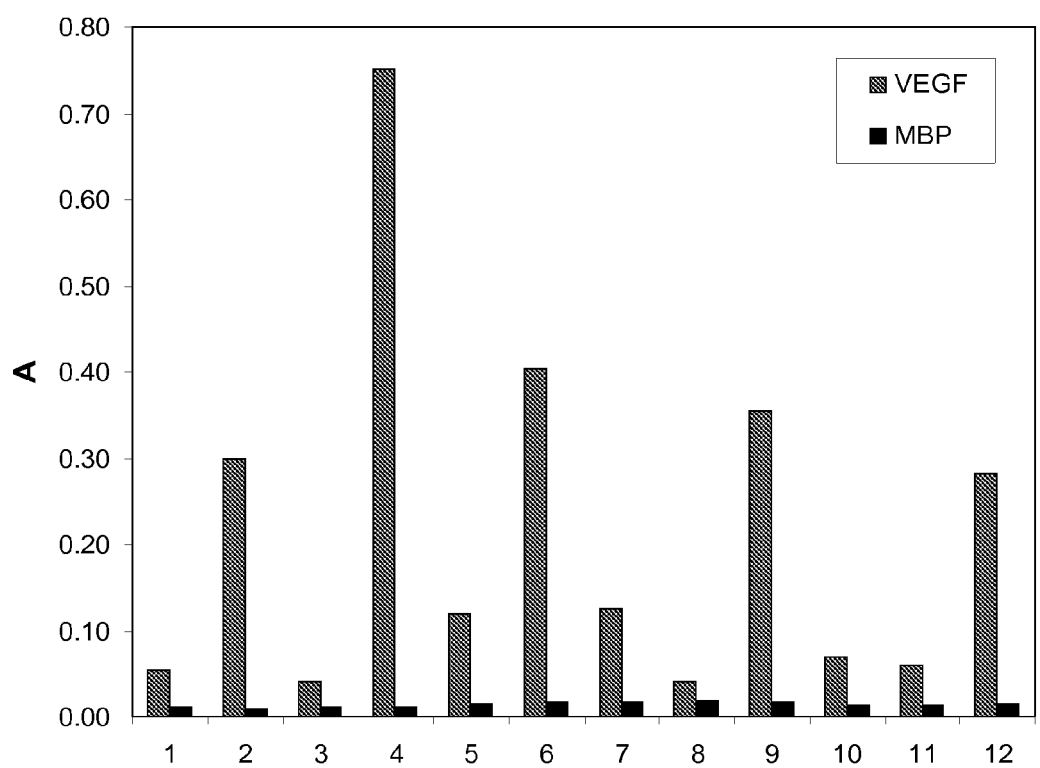
FIG. 1. Specific dog VEGF-A164 binding of selected designed ankyrin repeat proteins.
Figure 2A:
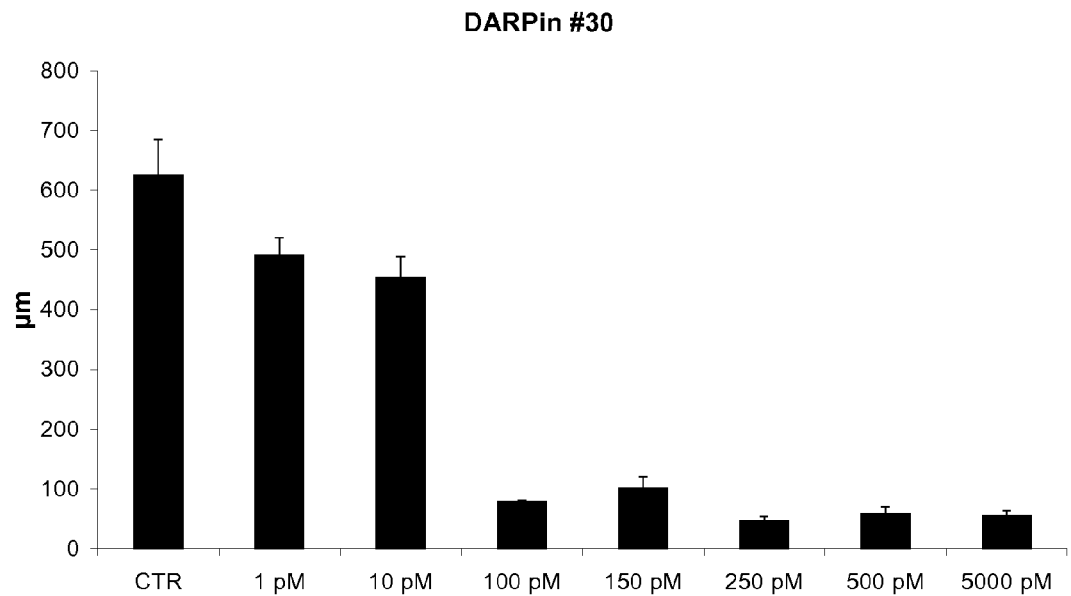
Figure 2B:
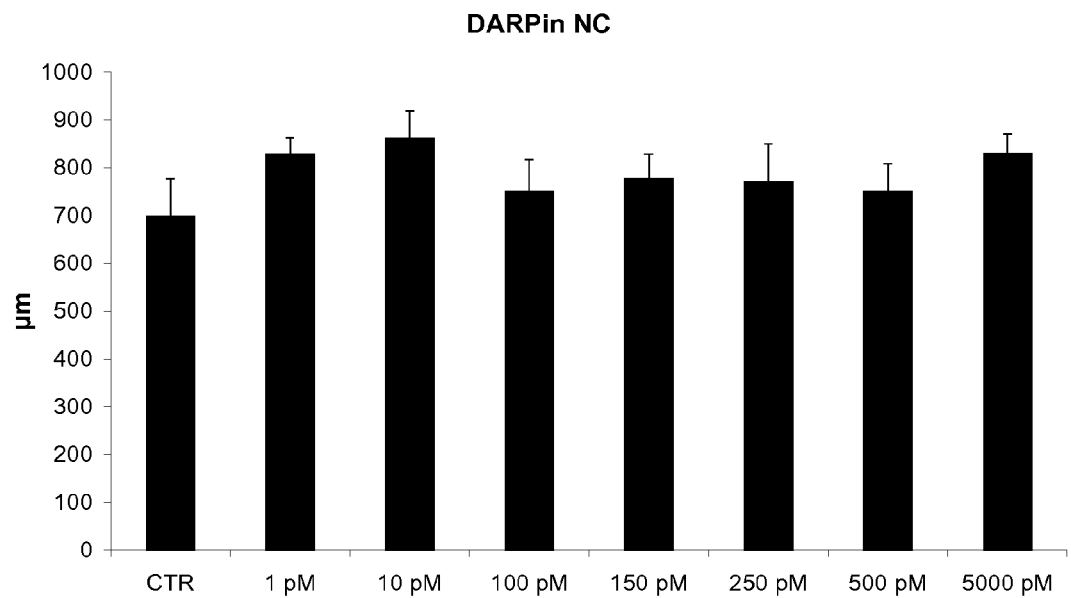

The results from two example spheroid sprouting assays are shown in FIG. 2a (DARPin #30 with binding specificity for VEGF-Axxx) and FIG. 2b (DARPin NC, a negative control DARPin with no binding specificity for VEGF-Axxx; e.g. DARPin E3_5 (Binz et al., 2005, loc. cit.). The best performing DARPins in this assay showed IC$_{50}$ values in the range of 10 to 50 pM, while AVASTIN® (bevacizumab), LUCENTIS® (ranibizumab), and MACUGEN® (pegaptamib) showed IC$_{50}$ values in parallel experiments in the range of 150 and 500 pM.

Example 3

Determination of the Target Specificity of DARPin #27 in Comparison to Avastin® by Surface Plasmon Resonance Analysis Dog VEGF-A164 or Dog VEGF-A164b were immobilized in a flow cell and the interaction of DARPin #27 (the repeat domain of SEQ ID NO:1, corresponding to amino acids 1 to 159) and Avastin® with the immobilized targets were analyzed.

Surface Plasmon Resonance (SPR) Analysis

SPR was measured using a ProteOn instrument (BioRad). The running buffer was 20 mM HEPES, pH 7.4, 150 mM NaCl and 0.005% Tween 20. About 1200 RU of dog VEGF-A164 or dog VEGF-A164b were immobilized on a GLC chip (BioRad). The interactions were measured at a flow of 60 μl/min with 5 min buffer flow, 100 seconds injection of Avastin® or DARPin #27 at a concentration of 250 nM and an off-rate measurement of a few minutes with buffer flow. The signal of an uncoated reference cell was subtracted from the measurements.

Figure 3A:
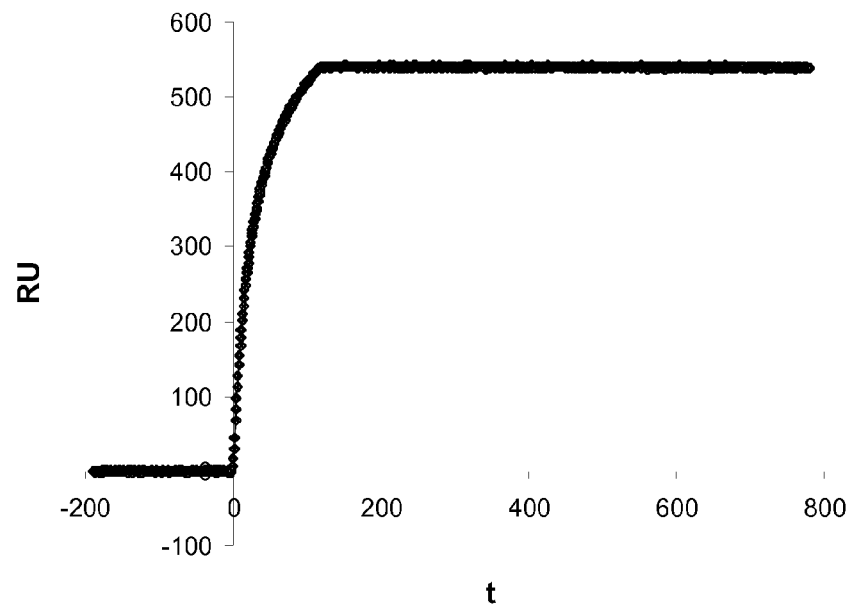
Figure 3B:
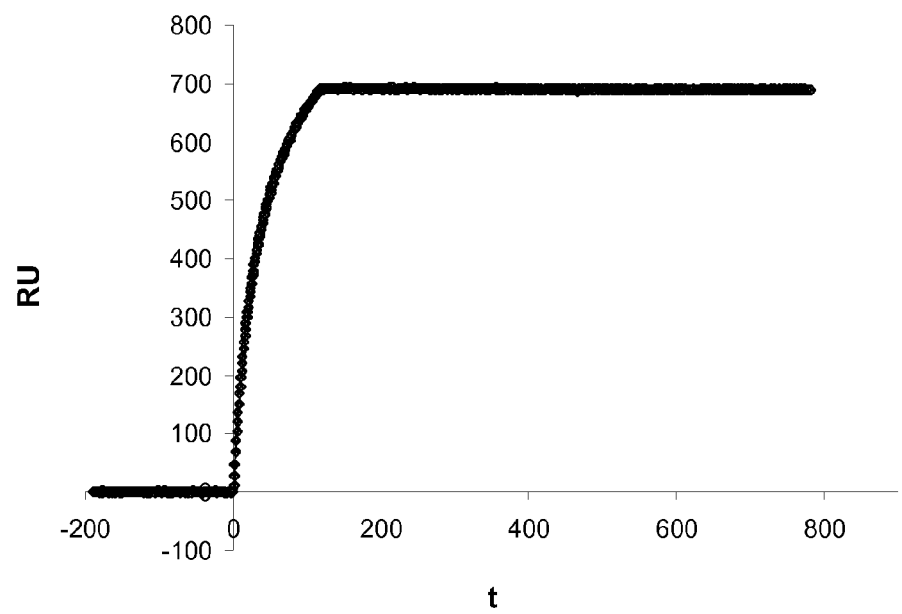
Figure 3C:
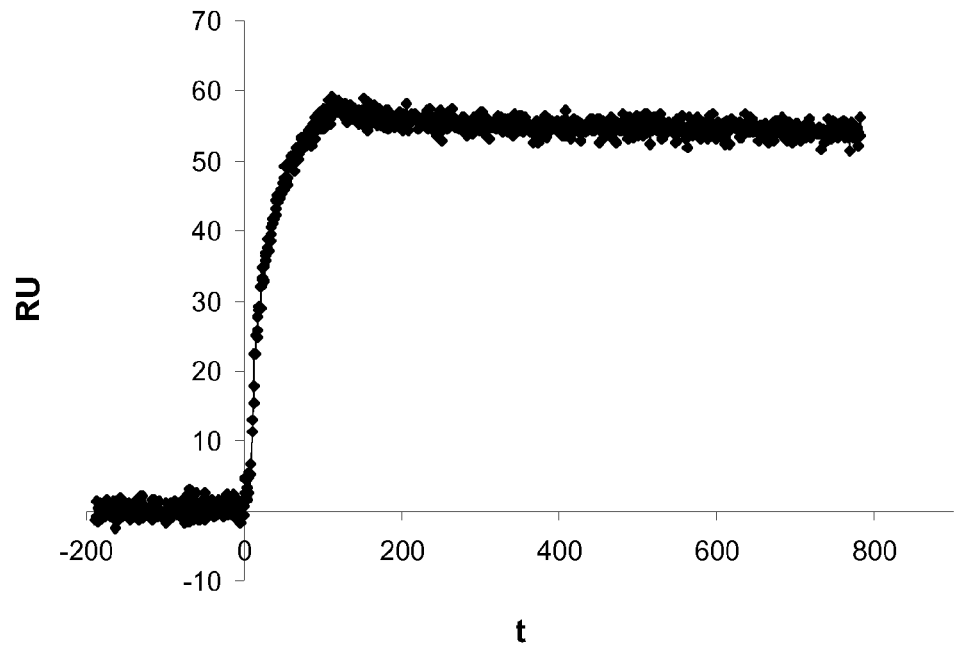
Figure 3D:
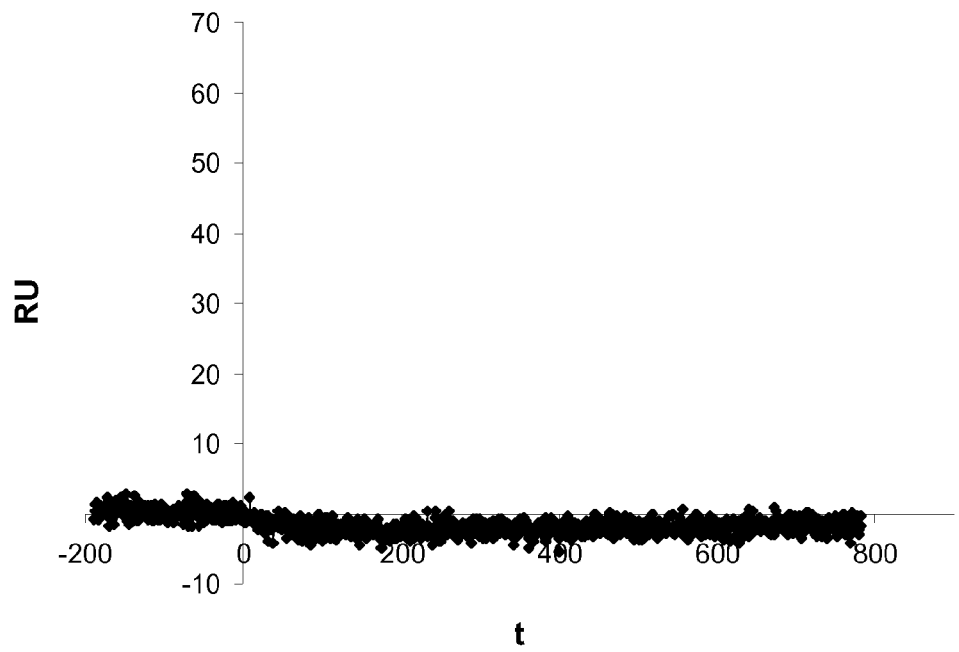

The results are shown in FIG. 3a (Avastin interaction with dog VEGF-A164), FIG. 3b (Avastin interaction with dog VEGF-A164b), FIG. 3c (DARPin #27 interaction with dog VEGF-A164) and FIG. 3d (DARPin #27 interaction with dog VEGF-A164b). Whereas Avastin clearly interacts with both immobilized VEGF isoforms, the DARPin #27 shows only interaction with VEGF-A164 and not VEGF-A164b.

Example 4

In Vivo Efficacy of DARPin #30 in Inhibiting VEGF-A165 in a Vascular Leakage Rabbit Model Pegylated DARPin #30 (the repeat domain of SEQ ID NO:4 corresponding to the amino acids 1 to 126) or LUCENTIS® (ranibizumab) is applied by intravitreal injection into an eye of a rabbit to test their efficacy to inhibit vascular leakage induced by a subsequent intravitreous injection of human VEGF-A165.

Vascular Leakage Inhibition Measurements in Rabbits

At day 1 either PBS, PEGylated DARPin #30 (125 μg) or the equimolar amount of LUCENTIS® (ranibizumab) (162 μg) is applied by an intravitreal injection into one eye of each rabbit (treated eye). At day 4 or day 30 the treated eye of each rabbit was challenged by intravitreal injection of 500 ng of human VEGF-A165. Both eyes of all animals were evaluated 48 hours after the VEGF-A165 injection by measuring the fluorescein content in all eyes 1 h after intravenous injection of sodium fluorescein (50 mg/kg animal body weight, 10% (w/v) in 0.9% (w/v) saline solution). The ratios of the amounts of fluorescence in the treated and untreated eyes were calculated for every animal. A ratio of one corresponds to absence of additional fluorescence leakage in the treated eye, a ratio greater than one indicates more fluorescence leakage in the treated eye than in the untreated control eye.

Preparation of PEGylated DARPin

The PEGylation of protein by making use of a single Cys residue and maleimide chemistry is well known to the person skilled in the art and can be performed according to established protocols (e.g. from Pierce). DARPin #30 comprising an additional C-terminal linker (GGGSGGGSC, SEQ ID NO:8) was purified to near homogeneity using standard chromatographic methods. The protein is completely reduced using DTT and purified by gel-filtration to remove the DTT and to exchange the buffer by PBS. PEG-maleimide (methoxy-poly(ethylene glycol)-oxopropylamino-propyl maleimide; NOF, no. Sunbright ME-200MA) dissolved in PBS is mixed with the DARPin in PBS at about 15% molar excess of PEG-maleimide for 2-4 hours at room temperature. The PEGylated DARPin is then separated from non-reactive DARPin and non-reactive PEG moieties by using standard anion exchange chromatography.

The results are shown in FIG. 4. Both PEGylated DARPin #30 and LUCENTIS® (ranibizumab) were able to protect the rabbit eye from VEGF-A165 induced vascular leakage 4 days after they were applied by intravitreal injections. Nevertheless, only the PEGylated DARPin #30, and not LUCENTIS® (ranibizumab), was able to protect the rabbit eye from VEGF-A165 induced vascular leakage up to 30 days after the intravitreal injection.

In other experiments the intravitreal terminal half-lives of the different binding proteins of the invention were measured after intravitreal injections into rabbit eyes. DARPin #30 comprising an additional C-terminal linker (GGGSGGGSC, SEQ ID NO:8) was conjugated to a 20 kDa and a 40 kDa non-proteinaceous PEG moiety using the respective maleimide PEGs from NOF (see Example 5). The terminal half-lives were determined to be 3.5 days (+/−0.3 days), 6.1 days (+/−1.0 days) and 5.4 days (+/−0.8 days) for the DARPin #30, the DARPin #30 conjugated to the 20 kDa PEG moiety and the DARPin #30 conjugated to the 40 kDA PEG moiety. Surprisingly, increasing the molecular weight of the non-proteinaceous PEG moiety from 20 kDa to 40 kDa did not result in an increased terminal half-live. The same trend was observed in corresponding experiments were binding proteins comprising the repeat domain of SEQ ID NO:1 (amino acids 1 to 159) or SEQ ID NO:3 (amino acids 1 to 126) instead of the repeat domain of SEQ ID NO:4 were used.

Example 5

Recombinant Binding Proteins

Examples of recombinant binding proteins comprising a repeat domain binding VEGF-Axxx and a proteinaceous polymer moiety are SEQ ID NO:1 and 4. The repeat domain of SEQ ID NO:1 corresponds to amino acids 1 to 159 and the proteinaceous polymer moiety of SEQ ID NO:1 corresponds to amino acids 160 to 1'024. The repeat domain of SEQ ID NO:4 corresponds to amino acids 1 to 126 and the proteinaceous polymer moiety of SEQ ID NO:4 corresponds to amino acids 127 to 536.

The binding proteins of SEQ ID NO:1 and 4 were expressed in the cytoplasm of *Escherichia coli* using standard techniques known to the person skilled in the art (see, for example, the pQE expression system from Qiagen (Germany)). The Met residue additionally encoded by the expression vector was efficiently cleaved off in the cytoplasm of *E. coli* from the expressed polypeptide since the start Met is followed by a small Gly residue (i.e. the amino acid at position 1 of SEQ ID NO:1 and 4). The cells were lysed (e.g. by using a French press) and the binding proteins were purified to near homogeneity from the crude cell extract by using standard chromatographic techniques known to the person skilled in the art.

Examples of recombinant binding proteins comprising one repeat domain binding VEGF-Axxx and one non-proteinaceous polymer moiety were produced using the repeat proteins of SEQ ID No:2, 3, 5, 6, and 7. These repeat proteins comprise an N-terminal repeat domain, followed by a polypeptide linker and a C-terminal Cys. The respective repeat domains correspond to amino acids 1 to 159 for SEQ ID NO:2 and 7, and to amino acids 1 to 126 for SEQ ID NO:3 to 6. The repeat proteins of SEQ ID NO:2, 3, 5, 6, and 7 were expressed in the cytoplasm of *Escherichia coli* using standard techniques known to the person skilled in the art (see, for example, The Expressionist from Qiagen (Germany)). The Met residue additionally encoded by the expression vector was efficiently cleaved off in the cytoplasm of *E. coli* from the expressed polypeptide since the start Met is followed by a small Gly residue (i.e. the amino acid at position 1 of SEQ ID NO:2, 3, 5, 6, and 7). The cells were lysed (.e.g. by using a French press) and the binding proteins were purified to near homogeneity from the crude cell extract by using standard chromatographic techniques known to the person skilled in the art.

The purified repeat proteins comprising a single Cys residue were then conjugated to a non-proteinaceous polymer moiety using standard maleimide chemistry as outlined in Example 4. Thereby, a binding protein of the invention comprising the repeat protein of SEQ ID NO:2 and a 40 kDa non-proteinaceous PEG moiety (e.g. a 40 kDa maleimide-PEG ($\alpha$-[3-(3-maleimido-1-oxopropyl)amino]propyl-$\omega$-methoxy-polyoxyethylene) from NOF, product no. Sunbright ME-400MA), the repeat protein of SEQ ID NO:3 and a 20 kDa non-proteinaceous PEG moiety (e.g. a 20 kDa maleimide-PEG ($\alpha$-[3-(3-maleimido-1-oxopropyl)amino]propyl-$\omega$-methoxy-polyoxyethylene) from NOF, product no. Sunbright ME-200MA), the repeat protein of SEQ ID NO:5 and a 12 kDa non-proteinaceous PEG moiety (e.g. a 12 kDa maleimide-PEG ($\alpha$-[3-(3-maleimido-1-oxopropyl)amino]propyl-$\omega$-methoxy-polyoxyethylene) from NOF, product no. Sunbright ME-120MA), the repeat protein of SEQ ID NO:6 and a 5 kDa non-proteinaceous PEG moiety (e.g. a 5 kDa maleimide-PEG ($\alpha$-[3-(3-maleimido-1-oxopropyl)amino]propyl-$\omega$-methoxy-polyoxyethylene) from NOF, product no. Sunbright ME-050MA) and the repeat protein of SEQ ID NO:7 and a 2 kDa non-proteinaceous PEG moiety (e.g. a 2 kDa maleimide-PEG ($\alpha$-[3-(3-maleimido-1-oxopropyl)amino]propyl-$\omega$-methoxy-polyoxyethylene) from NOF, product no. Sunbright ME-020MA) were produced. The PEGylated repeat proteins were then further separated from non-PEGylated repeat proteins and excess PEG by standard chromatographic techniques known to the person skilled in the art.

Thus, SEQ ID NO:2, 3, 5, 6, and 7 were conjugated at the thiol of their C-terminal cysteine to a maleimide PEG ($\alpha$-[3-(3-maleimido-1-oxopropyl)amino]propyl-$\omega$-methoxy-polyoxyethylene). The following structure was thereby produced:

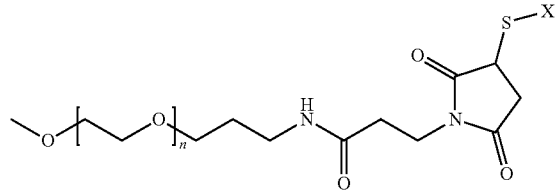

wherein X is SEQ ID NO: 2, 3, 5, 6, or 7; and n is a positive integer.

The invention claimed is:

1. A modified recombinant binding protein comprising an ankyrin repeat domain comprising the amino acids 1 to 126 of SEQ ID NO: 3 and a polyethylene glycol of at least 5 kDa molecular weight.

2. The binding protein of claim 1, wherein said ankyrin repeat domain is conjugated at its C-terminus via a peptide bond to a polypeptide linker consisting of 2 to 24 amino acids and having a C-terminal Cys residue, wherein the thiol of said C-terminal Cys is further conjugated to a maleimide-coupled polyethylene glycol.

3. The binding protein of claim 2, wherein said maleimide-coupled polyethylene glycol is α-[3-(3-maleimido-1-oxopropyl)amino]propyl-ω-methoxy-polyoxyethylene.

4. The binding protein of claim 2, wherein said polyethylene glycol has a molecular weight of 20 kDa.

5. The binding protein of claim 1 comprising the amino acid sequence of SEQ ID NO: 3, wherein the thiol of the C-terminal Cys of SEQ ID NO: 3 is further conjugated to a maleimide-coupled polyethylene glycol.

6. The binding protein of claim 5 wherein said maleimide-coupled polyethylene glycol is α-[3-(3-maleimido-1-oxopropyl)amino]propyl-ω-methoxy-polyoxyethylene, and wherein the polyethylene glycol has a molecular weight of at least 10 kDa.

7. A pharmaceutical composition comprising the binding protein of claim 1 and optionally a pharmaceutical acceptable carrier and/or diluent.

* * * * *